(12) United States Patent
Wright et al.

(10) Patent No.: US 11,771,586 B2
(45) Date of Patent: *Oct. 3, 2023

(54) THERMAL CONTRAST THERAPY DEVICE

(71) Applicant: Solid State Cooling Systems, Inc, Wappingers Falls, NY (US)

(72) Inventors: Lloyd Wright, Hopewell Junction, NY (US); Vishesh Nandedkar, Poughkeepsie, NY (US); John Cuatt, Wappinger Falls, NY (US)

(73) Assignee: Solid State Cooling Systems, Inc, Wappingers Falls, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/592,789

(22) Filed: Feb. 4, 2022

(65) Prior Publication Data

US 2022/0331151 A1 Oct. 20, 2022

Related U.S. Application Data

(63) Continuation of application No. 17/204,405, filed on Mar. 17, 2021, now Pat. No. 11,266,523, which is a continuation-in-part of application No. 15/867,238, filed on Jan. 10, 2018, now abandoned.

(60) Provisional application No. 62/444,416, filed on Jan. 10, 2017.

(51) Int. Cl.
*A61F 7/00* (2006.01)
*A61F 7/02* (2006.01)

(52) U.S. Cl.
CPC .................. *A61F 7/00* (2013.01); *A61F 7/02* (2013.01); *A61F 2007/0054* (2013.01); *A61F 2007/0056* (2013.01); *A61F 2007/0093* (2013.01); *A61F 2007/0096* (2013.01)

(58) Field of Classification Search
CPC ...... A61F 2007/0054; A61F 2007/0056; A61F 2007/0093; A61F 2007/0096; A61F 7/0085

See application file for complete search history.

(56) References Cited

U.S. PATENT DOCUMENTS

| 5,072,875 | A | 12/1991 | Zacoi |
| 11,266,523 | B2 * | 3/2022 | Wright ...................... A61F 7/02 |
| 2008/0071330 | A1 | 3/2008 | Quisenberry et al. |
| 2012/0179230 | A1 | 7/2012 | Barrones et al. |
| 2013/0006335 | A1 | 1/2013 | Lowe |

(Continued)

*Primary Examiner* — Kaitlyn E Smith
(74) *Attorney, Agent, or Firm* — TRACNIK LAW PLLC; Joseph P. Kincart

(57) ABSTRACT

Methods and apparatus for an improved Contrast Therapy Device that delivers alternating heated and chilled temperature fluids to a contrast thermal therapy pad. Mitigation processes maintain water temperature in hot water tanks and cold water tanks in order to keep water temperatures in the respective tanks from drifting beyond a desired setpoint range when the system switches a therapy state from a cooling cycle to a heating cycle or from heating cycle to a cooling cycle. Thermal shock is reduced to the fluid tanks. Mitigation techniques include delaying actuation of a return path flow, such as via a diverting solenoid. Mitigating delay can be a static time delay based upon one or both of: a volume of water in a therapy pad and related volume and rate of flow; and meeting a threshold transition temperature for return fluid temperature.

20 Claims, 15 Drawing Sheets

(56) References Cited

U.S. PATENT DOCUMENTS

| | | |
|---|---|---|
| 2013/0238042 A1 | 9/2013 | Gildersleeve et al. |
| 2014/0222121 A1 | 8/2014 | Spence et al. |
| 2015/0118107 A1 | 4/2015 | Sunkara et al. |
| 2015/0335468 A1 | 11/2015 | Rose et al. |
| 2016/0022477 A1 | 1/2016 | Schaefer et al. |
| 2016/0022478 A1 | 1/2016 | Schaefer et al. |
| 2016/0242957 A1 | 8/2016 | Schaefer et al. |
| 2017/0348449 A1 | 12/2017 | Ward et al. |

\* cited by examiner

THERMAL CONTRAST THERAPY DEVICE

CROSS-REFERENCE TO RELATED APPLICATIONS

This application is a continuation of U.S. patent application Ser. No. 17/204,405, titled "THERMAL CONTRAST THERAPY DEVICE", filed on Mar. 17, 2021, which in turn claimed priority to U.S. Non Provisional patent application Ser. No. 15/867,238 titled "ACCELERATED TRANSITION THERMAL CONTRAST THERAPY DEVICE", filed on Jan. 10, 2018, which in turn claimed the benefit of U.S. Provisional Patent Application Ser. No. 62/444,416, titled "ACCELERATED TRANSITION THERMAL CONTRAST THERAPY DEVICE", filed on Jan. 10, 2017, the entire content of each of which is hereby incorporated by reference in its entirety.

FIELD OF THE INVENTION

The present invention relates to a thermal device and system for therapy to biological tissue. The apparatus and methods disclosed herein provide for improved accelerated transitions between a heating cycle and cooling cycle applied to biological tissue by way of a hydraulic pad placed in thermal proximity to tissue being treated, as well as compression of tissue being treated based upon controlled variation of a fluid pressure within the hydraulic pads in thermal proximity to an area of treated biological tissue.

BACKGROUND OF THE INVENTION

Studies have shown that cooling and heating, along with cyclical compression, can speed muscle recovery after strenuous activity. In thermal therapy applications, there is a need to precisely control temperatures in microenvironments. Conventional cooling devices employed either ice baths or the evaporation and condensation of gases, such as chlorofluorocarbon (CFC) and hydrochlorofluorocarbon (HCFC) to transfer heat. However, these substances are not environmentally friendly, as they are known to damage the earth's ozone layer and have a high global warming potential that can be thousands of times the potential of carbon dioxide. Accordingly, solid state cooling systems were developed that allow production of small commercial packages that are capable of precise temperature control in a variety of applications. Further, the solid state cooling systems reduce energy usage considerably, thereby providing additional cost-savings to users.

Currently, many trainers and therapists use ice wraps for cooling and heated hydroculator pads for heating. The problem with these methods is the lack of temperature control. The ideal temperature for cooling muscles and joints is 5-10° C. and for heating it is 45-48° C. Ice is much colder than this, typically coming out of a freezer at −18C and warming to 0° C. when melting, cold enough to cause frostbite if enough layers of fabric are not placed between the patient's skin and the ice. Hydroculators recommended set points are 160-165° F., 71-74° C., (Chattanooga Hydroculator M2 manual set point range), way above the 49° C. maximum temperature skin should come in contact with. As a result, hot and cold therapy injuries are common because users often fail to place enough layers of insulating fabric between the skin and the wrap/pad.

Thermal contrast therapy devices have been known to use a single reservoir from which fluid is withdrawn and either heated or cooled. These solid state cooling systems employ fluids to transfer heat from microenvironments that require temperature control. However, currently available systems suffer from several drawbacks, including the following: a) the known systems do not rapidly transition between heating and cooling. The lack of rapid transition greatly lengthens the time required for therapy, and may reduce therapeutic effectiveness; b) known systems such as the '914 patent use compressed air to provide compression. The air compressors used are cumbersome, noisy and may be irritating to a user; c) the known systems are designed to be carried over a patient's shoulder, which is conspicuous to nearby persons. For patients desiring anonymity when requiring therapy (e.g., professional athletes), such conspicuousness can be a significant detriment; d) unless frequently cleaned (or unless toxic coolants are used) the known systems allow bacteria and other microbes to grow in fluid channels of current systems, creating a potential health hazard.

SUMMARY OF THE INVENTION

Accordingly, the present invention provides methods and apparatus for an improved Contrast Therapy Device that delivers alternating heated and chilled temperature fluids to a contrast therapy pad that is placed in thermal proximity to tissue being treated. The improved methods and apparatus include mitigation processes that are deployed to maintain respective fluid temperatures in a separate heated fluid storage tank and chilled fluid storage tank for controlled circulation through a thermal therapy pad; and efficient drainage of a thermal therapy pad for storage while not in use. Fluid stored in a storage tank and circulated through a thermal therapy pad may include, for example, an aqueous solution.

The mitigation processes used to maintain respective water temperatures reduce thermal shock to a fluid storage tank resulting from a system switching a therapy state of a contrast therapy pad from a cooling cycle to a heating cycle, or from heating cycle to a cooling cycle. The apparatus and methods of the improved contrast therapy system keep water temperatures in a respective heated fluid storage tank and a chilled fluid storage tank from drifting outside of threshold setpoint ranges desired for each fluid storage tank.

Methods and apparatus presented herein for reducing thermal shock to a respective fluid storage tank include delaying actuation of a return path flow, such as via a diverting solenoid. This delay can be a static time delay based upon one or more of: a volume of fluid in a therapy pad; a related volume and rate of flow of circulated fluid; and a threshold transition temperature for return fluid temperature being met.

The present invention, overcomes the shortcomings noted above, by use of a flexible apparatus to provide a fast transition thermal therapy to biological tissue with predefined temperature and pressure cycles, temperature controlled fluids, and pressurized wraps. Various features and embodiments are further described in the following figures, drawings, and claims.

One general aspect of the present invention includes a contrast therapy apparatus to provide controlled therapeutic treatments via a thermal pad delivering one or more cycles of thermal conditions to a body part. The apparatus may include a thermal pad or other fluid delivery mechanism with a fluidic channel having an input port and an output port; and a thermally-transmissive outer covering. The contrast therapy apparatus may also include a control unit, including: a fluid channel output port coupled to the input port of the thermal pad fluidic channel; a fluid channel input port coupled to the output port of the thermal pad fluidic channel; a hot-fluid circulation loop coupled to the output port and the input port; a cold-fluid circulation loop coupled to the output port and the input port; a hot-fluid reservoir coupled to the hot-fluid circulation loop, to hold hot fluid to be circulated in the hot-fluid circulation loop; a cold-fluid reservoir coupled to the cold-fluid circulation loop, to hold cold fluid to be circulated in the cold-fluid circulation loop; a pump to provide fluid flow in at least one of the hot-fluid circulation loop and the cold-fluid circulation loop; a temperature sensor; a processor coupled to a memory, the processor configured to execute instructions stored in the memory, to provide to the thermal pad a fluid flow having a predetermined temperature profile; and one or more diverting valves operative to cause the hot fluid to flow out of the hot reservoir and into the thermal pad, and flow out of the thermal pad into a cold fluid reservoir during a cold to hot transition delay period, and the hot fluid to flow out of the hot reservoir and into the thermal pad, and flow out of the thermal pad into the hot fluid reservoir during a hot cycle that follows the cold to hot transition delay period.

Various implementations and embodiments may include one or more of the following features. The contrast therapy apparatus may further include separate pumps for the hot-fluid circulation loop and the cold-fluid circulation loop. One or more diverting valves may include one or more hot valves to couple the hot-fluid circulation loop to the therapy pad and one or more cold valves to couple the cold-fluid circulation loop to the therapy pad, said one or more hot valves and one or more cold valves operative to cause the cold fluid to flow out of the cold reservoir and into the thermal pad, and flow out of the thermal pad into the hot fluid reservoir during a hot to cold transition delay period, and the cold fluid to flow out of the cold reservoir and into the thermal pad, and flow out of the thermal pad into the cold fluid reservoir during a cold thermal cycle which follows the hot to cold transition delay period. A flow of cold fluid may progress out of the cold reservoir and into the thermal pad, and flow out of the thermal pad into the hot fluid reservoir during a hot to cold transition delay period improves the stability of the cold fluid reservoir during a cold thermal cycle by reducing a change of temperature change in the cold fluid reservoir as compared to a change in temperature in the cold fluid reservoir without a transition delay period including returning fluid from the cold fluid reservoir into the hot fluid reservoir. One or both of the hot transition delay period and the cold transition delay period may be based upon a size of the thermal pad. A delay period includes between 5 seconds and 90 seconds. and preferably includes a delay period of between 15 seconds and 40 seconds.

In some embodiments, a flow rate of fluid through the thermal pad may be between about 0.5 to 2 liters per minute, and some preferred embodiments may include a flow rate of fluid through the thermal pad of between about 0.8 and 1.2 liters per minute.

Some embodiments may include a delay time determined by measuring a returning fluid temperature and actuating return side diverting valves when the measured return side temperature reaches a pre-determined threshold. The predetermined threshold occurs when return side temperature changes in an amount of between about 2c and 20c from a normal return side treatment temperature. The pre-determined threshold occurs when return side temperature changes in an amount of between about 7c and 13c from a normal return side treatment temperature. The contrast therapy apparatus where the delay period is determined by measuring temperature of returning fluid and actuating return side diverting valves when the measured return side temperature change meets a pre-determined rate of change. The pre-determined rate of change is between about 0.01 c/sec and 0.2 c/sec. The pre-determined rate of change is between about 0.01 c/sec and 2.0 c/sec. The pre-determined rate of change is between about 0.5 c/sec and 1.5 c/sec.

One or both of the hot transition delay period and the cold transition delay period may be based upon a type of thermal pad through which fluid is circulated. A flow of hot fluid out of the hot reservoir and into the thermal pad, and flow out of the thermal pad into the cold fluid reservoir during a cold to hot transition delay period improves stability of the hot fluid reservoir during a hot thermal cycle by reducing a change of temperature change in the hot fluid tank as compared to a change in a temperature in the hot fluid tank without a transition delay period including returning fluid from the hot fluid tank into the cold fluid reservoir.

Some implementations may include a contrast therapy apparatus including a solenoid valve at each end of therapy pad. The valves may be operative to divert fluid from flowing to the thermal pad to flowing to a venturi that provides suction pressure to remove fluid from the wrap. The contrast therapy apparatus may additionally include tubing attached to each valve, the tubing size including a inside diameter and a flow rate through the venturi is between about 1 liters per minute and 2 liters per minute. In some embodiments, a suction pressure generated may preferably be between about 1 pound per second and 2 pounds per second. Aspects of various implementations of the described techniques may include hardware, a method or process, or computer software.

BRIEF DESCRIPTION OF THE DRAWINGS

As presented herein, various embodiments of the present invention will be described, followed by some specific examples of various components that can be utilized to implement the embodiments. The following drawings facilitate the description of some embodiments of the present invention.

Figure 1:
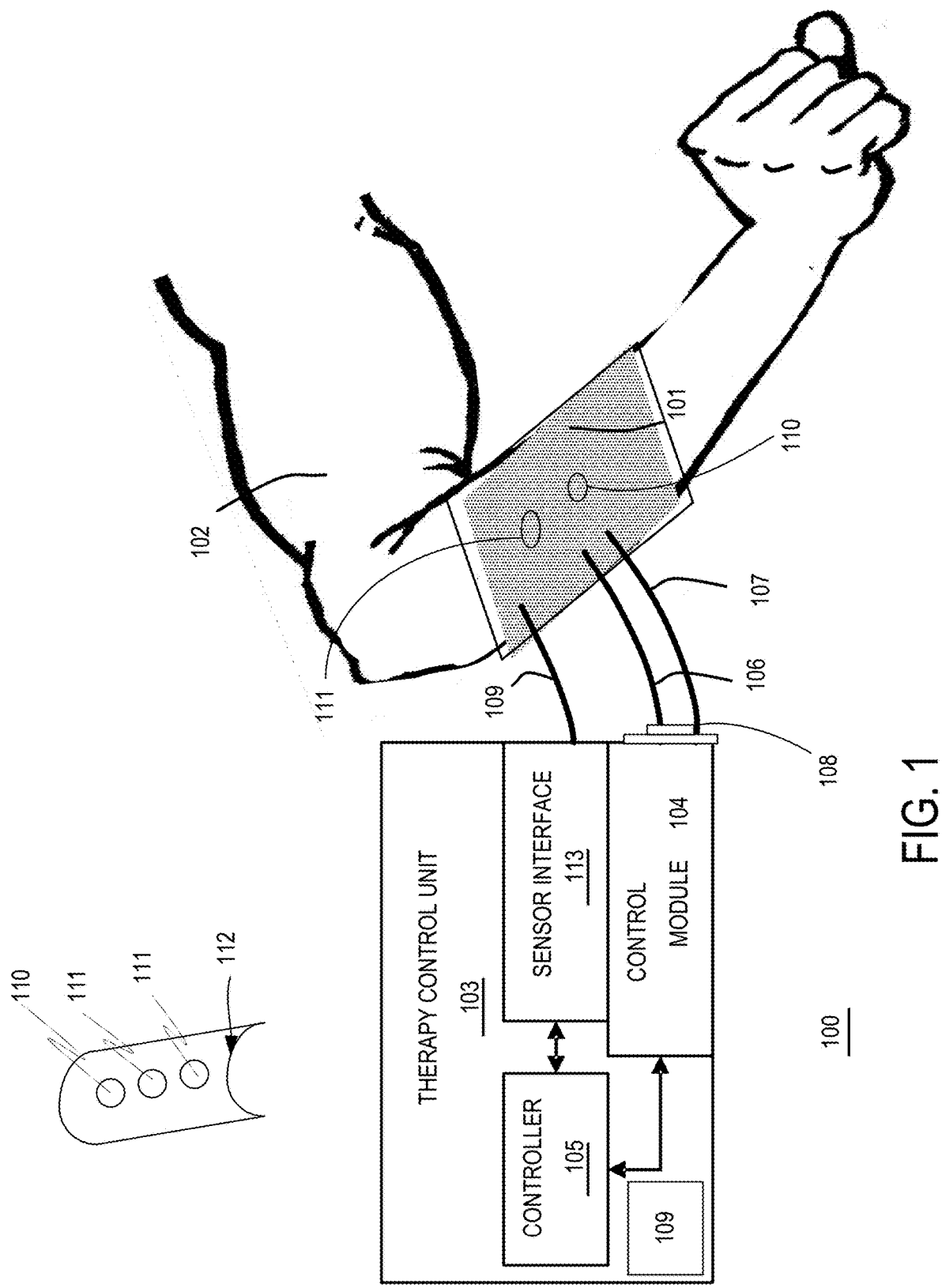
FIG. 1 illustrates at a relatively high level of abstraction a thermal contrast therapy system according to some exemplary embodiments of the present invention.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures. Optional portions of the figures may be illustrated using dashed or dotted lines, unless the context of usage indicates otherwise.

DETAILED DESCRIPTION

The present invention provides apparatus and methods for providing rapid thermal transition during thermal contrast therapy, and compression therapy for biological tissue. According to the present invention, thermal treatment is provided via a precisely controlled thermal fluid that is circulated in thermal proximity to biological tissue being treated. A hydraulic wrap simultaneously provides compression to the biological tissue receiving thermal treatment. Methods and apparatus for an improved Contrast Therapy Device that delivers alternating heated and chilled temperature fluids to a contrast thermal therapy pad. Mitigation processes maintain water temperature in hot water tanks and cold water tanks in order to keep water temperatures in the respective tanks from drifting beyond a desired setpoint range when the system switches a therapy state from a cooling cycle to a heating cycle or from heating cycle to a cooling cycle. Thermal shock is reduced to the fluid tanks. Mitigation techniques include delaying actuation of a return path flow, such as via a diverting solenoid. This delay can be a static time delay based upon one or both of: a volume of water in a therapy pad and related volume and rate of flow and/or meeting a threshold transition temperature for return fluid temperature.

In some embodiments, sensors may provide a feedback loop to ascertain one or more physical conditions associated with the thermal and compression therapy. In some aspects, sensors quantify a condition being experienced by the treated tissue. Data generated by the sensors may be received by a controller which in turn provides a control command to apparatus providing one or both of: thermal energy to the thermal fluid being circulated in thermal proximity to the tissue and a pump proving hydraulic pressure within a compression wrap fixedly and removably attached in an area surrounding the tissue being treated. Data generated may also be used to ascertain compliance with a prescribed protocol and memorialize a time, date, and place of compliance with a thermal contrast treatment protocol, as well as conditions of the compliance.

In some embodiments, a thermal contrast treatment protocol may be stored on a Smart Device and communicated to a controller for administration to a patient. In return, the controller may communicate back to the smart device, data descriptive of actual conditions experienced by a patient. A smart device may include, by way of non-limiting example, a mobile phone or tablet. The smart device may be equipped with GPS to ascertain a location, a clock to ascertain a time and date and near field communications, such as Bluetooth, WiFi, or ANT to communicate with the controller.

In another aspect, in some embodiments, multiple loops of thermal fluid may be included within a wrap and one or more of the loops may circulate thermal fluid at a given time. Similarly, a same or different loop for fluid within the wrap may be used to contain hydraulic pressure that in turn creates a compression force to tissue around which the hydraulic wrap is fixedly and removably attached.

According to the present invention, in some embodiments, a same hydraulic loop is used to circulate heated fluid during a first interval and chilled fluid during a second interval. In other embodiments, a first loop and a second loop may circulate fluid based upon the actuation of disparate first and second pumps in order to precisely and quickly transition from a temperature presented via a first fluid loop and a second fluid loop.

The exemplary systems and methods of this disclosure will be described in relation to software, firmware, modules, and associated hardware. However, to avoid unnecessarily obscuring the present disclosure, the following description omits well-known structures, components and devices that may be shown in block diagram form, are well known, or are otherwise summarized.

The present invention provides specific control to provide what an operator deems is optimum healing parameters and avoidance of injuries. The apparatus as disclosed herein provides precise temperature control at the skin, and also allows a thermal therapy wrap to be used to be temperature controlled and form-fitting to the body part being treated. The present invention also enables the ability to pump a temperature-controlled fluid through the wrap and providing good thermal contact through form-fitting to the skin.

The heat transfer mechanism for wraps/pads to skin is primarily through thermal conduction. The equation for calculating heat transfer through a flat surface via thermal conduction from Fourier's Law is as follows:

$$Q/A = k/L * DT$$

Where Q=heat transfer rate (watts)

a. A=area through which heat is transferred (meters$^2$)

b. k=thermal conductivity of the material through which heat is transferred (watts/meter °K)

c. L=thickness of the material through which heat is transferred d. DT=the temperature gradient across the material through which the heat is transferred When calculating heat transfer rates, where typically there are several layers of "thermal resistance", an electrical model is often used, where thermal resistances Θ are substituted for electrical resistances. For conduction, the thermal resistance Θ=L/K.

When several thermal resistances exist, the heat flux becomes
a. n $$Q/A=[S(1/\Theta)]^{-1}*(DT)$$

a. 1
b. Where
C. n
　i. (1/Θ=the sum of all layers (n) through which heat is transferred, so for three layers this
　　1. would be $(L_1/k_1+L_2/k_2+L_3\ k_3)$
d. Q/A=heat flux (heat transferred per unit area)

For a form-fitting wrap made from urethane coated Nylon such as SOFT TEX RF-200, the nylon is 0.28 mm thick. Nylon has a thermal conductivity k=0.25 w/m° K, so, the heat flux Q/A is:

$$\Theta=[(0.2\ mm/1000\ mm/m)/(0.25w/m°\ K)]=0.0008°\ Km^2/w$$

(The actual wrap contact area is much less than 1 square meter, and the skin and hair on the skin add additional resistance to heat transfer, so the actual heat flux into the body is less.)

In some embodiments, a Terry cloth towel may be used against skin of a patient, a thickness of a towel may be for example, about 4-8 mm and the thermal resistance of moist cotton fabric of 0.2 w/mK (this value varies with water content from 0.04-0.6) we calculate a heat flux of:

$$\Theta=[(0.0002/0.25)+(0.004/0.2)]=0.02°\ Km^2/w$$

Thus the thermal resistance of the form fitting wrap/pad is approximately ½5th that of the wrap with Terry cloth towel.

To calculate the overall heat flux, the heat transfer rate from the fluid flowing through the wrap/pad to the wrap/pad inner surface must be included.

The thermal resistance of flowing water over the inner surface of the wrap/pad depends upon the flow rate and the pad geometry, but is on the order of 0.01° $Km^2/w$. Thus, for a typical heating temperature gradient of 10° C. (37-47° C.)=10° C. (° K) between the inner wrap surface temperature and the skin, the heat flux can be estimated as follows:

For the formfitting wrap/pad: Q/A=$(0.01+0.0008)^{-1}*(10)$=930 w/$m^2$

While for a non-formfitting pad: Q/A=$(0.01+0.02)^{-1}*(10)$=330 w/$m^2$

The form-fitting pad has approximately 3 times the heat flux of the non-formfitting pad with the Terry cloth towel. As a result, to achieve the same heating, the temperature gradient from the non-formfitting pad to the skin must be three times greater, or 30° C. This is why Chattanooga recommends the Non-formfitting pad be heated to 71° C., 71-37=34° C. or about three times the temperature gradient.

The highest recommended temperature coming in contact with skin is 50° C., 71° C. can cause burns to skin, which is why injuries are common. Similar problems can occur when cooling with ice.

The present invention, the form-fitting wrap with fluid channels, seeks to prevent potential injuries by providing the same heating at much lower temperatures, less than 50° C. for heating and above 5° C. for cooling.

In some embodiments, insulative Neoprene backing to provide bladder support that focuses the bladders expansion onto the patient's body part, maximizing contact efficiency. Neoprene or a like material with an ability to match the body's contours is preferred. A localized mechanism for focusing compression on specific areas of the pad/body may be included in some embodiments and may include a strap with a hook and loop connector, a corset type cinch, buttons, snaps, buckle or other fastener may also be used.

Further, the examples disclosed are for exemplary purposes only and other examples may be employed in lieu of, or in combination with, the examples disclosed. It should also be noted that the examples presented herein should not be construed as limiting of the scope of embodiments of the present disclosure, as other equally effective examples are possible and likely. The scope of the invention is set forth in the issued claims and equivalents thereof.

As used herein, the term "module" refers generally to a logical sequence or association of steps, processes or components. For example, a software module may comprise a set of associated routines or subroutines within a computer program. Alternatively, a module may comprise a substantially self-contained hardware device. A module may also comprise a logical set of processes irrespective of any software or hardware implementation.

A module that performs a function also may be referred to as being configured to perform the function, e.g., a data module that receives data also may be described as being configured to receive data. Configuration to perform a function may include, for example: providing and executing sets of computer code in a processor that performs the function; providing configuration parameters that control, limit, enable or disable capabilities of the module (e.g., setting a flag, setting permissions, setting threshold levels used at decision points, etc.); providing or removing a physical connection, such as a jumper to select an option, or to enable/disable an option; attaching a physical communication link; enabling a wireless communication link; providing electrical circuitry that is designed to perform the function without use of a processor, such as by use of discrete components and/or non-CPU integrated circuits; setting a value of an adjustable component (e.g., a tunable resistance or capacitance, etc.), energizing a circuit that performs the function (e.g., providing power to a transceiver circuit in order to receive data); providing the module in a physical size that inherently performs the function (e.g., an RF antenna whose gain and operating frequency range is determined or constrained by the physical size of the RF antenna, etc.), and so forth.

Aspects of the present disclosure may be embodied as a system, method or computer program product. Furthermore, aspects of the present disclosure may take the form of a computer program product embodied in one or more computer readable medium(s) having computer readable program code embodied thereon or stored within a memory.

The present disclosure relates to methods and apparatus for maintaining temperature control of a body part. More specifically, the present disclosure presents methods and apparatus for a thermal contrast therapy system, including circulating thermal fluid in loops or channels through a pad or other item placed in thermal proximity to an area of a person or other mammal to be treated with the thermal therapy.

In some desirable embodiments, a thermal therapy system includes the following attributes: it provides rapid switching from heating with a thermal therapy pad to cooling with a thermal therapy pad; it has programmable temperature and time cycles for therapy provided through the thermal therapy pad, it provides cyclical compression without irritating noise associated with an air compressor; cyclical thermal cycling and compression is user programmable; it is lightweight enough to be easily carried by a thermal therapy patient and may be carried inconspicuously; and it includes a built-in sterilizer mechanism to treat its fluid loop(s).

In the following sections, detailed descriptions of examples and methods of the disclosure are given. Description of both preferred and alternative examples, though thorough, are exemplary only, and it is understood that variations, modifications, and alterations may be apparent to those skilled in the art, and such variations, modifications, and alterations are within the scope of the present invention. It is therefore to be understood that any examples included herein do not limit the broadness of the aspects of the underlying disclosure as defined by the claims.

FIG. 1 illustrates at a relatively high level of abstraction a Thermal Contrast Therapy System 100 according to the present invention that is operative to administer heating therapy; cooling therapy; and in some embodiments, pressure therapy. Thermal Contrast Therapy System 100 includes a therapy pad 101 coupled to a Therapy Control Unit 103. Therapy pad 101 is illustrated affixed to a body portion 102, such as an arm (other body parts may also be treated with thermal therapy according to the present invention). Therapy pad 101 may be fashioned or adaptable to fit or conform to be placed in thermal proximity to a variety of body parts. For example, therapy pad 101 may be a wrap removably fixed in position around a portion of a limb such as an arm (as illustrated in FIG. 1); leg; torso, foot, hand; neck, skull; or other body portion. Alternatively, therapy pad 101 may be a substantially flat pad and suitable for removably fixing to a shoulder or a back. Still further embodiments include a therapy pad 101 that is cap-shaped to fit on the head, boot shaped to fit over a foot, mitten shaped to fit over hand, and so forth. In some embodiments, therapy pad 101 may be flexible to accommodate being placed over a joint such as a knee; elbow; or ankle and be able to flex as the joint is flexed.

Therapy pad 101 may be coupled to a body part either securely or loosely. For example, a secure coupling may use straps to couple therapy pad 101 to a body portion 102 such as a lower back. A secure coupling may include snaps or a hook and loop fastener such as Velcro™ if therapy pad 101 is fashioned as a wrap around a limb. In other embodiments, a therapy pad 101 may be loosely coupled if it merely rests upon a body part, such as a cap-shaped therapy pad 101 that may be placed on a head, or a therapy pad 101 that may be draped over a shoulder, and so forth. In some embodiments, therapy pad 101 may be adapted to be held in place by an external apparatus, e.g., if therapy pad 101 is placed inside a brace, or inside a compression sleeve, or the like.

Therapy Control Unit 103 may include a physical control module 104 that provides control via electrical current to one or more heating and/or cooling devices in thermal communication via fluid lines 107, 106 with therapy pad 101. For example, Therapy Control Unit 103 may include heaters and/or coolers to deliver a temperature-controlled fluid to therapy pad 101 (e.g., fluid line 106) and receive fluid returned from therapy pad 101 (e.g., via line 107). Therapy pad 101 may include an internal fluidic channels and connectors coupling fluid line 106 to line 107, such that a closed loop may be formed from fluid line 106, through therapy pad 101 and back to Therapy Control Unit 103 via fluid line 107.

In some embodiments, additional types of physical therapeutic conditions may be provided, such as a pressure stimulus delivered to the body portion 102 via therapy pad 101 and hydraulic pressure delivered via fluid line 106, e.g., by use of a pump 109 within the therapy control module 103 and a valve 108. The pump 109 and valve 108 may be used to create pressure within the fluid lines 106 107. The increased pressure may in turn cause increased compression force upon tissue in the body portion 102 around which the thermal pad 101 is secured. The increased pressure may be accomplished via Therapy Control Unit 103 increasing pump 109 performance. For example, a pump 109 may be used to force increased fluid into fluid line 106 and thereby increase pressure in the fluid line 106.

In another aspect, a valve 108 may divert some fluid to return line 107 and/or the valve 108 may partially close a return line 107 to prevent fluid from returning and thereby increase pressure within the line. Either method alone or in cooperation may be used to increase an internal pressure of fluid line 106, an internal pressure of line 107, and/or an internal pressure of a fluidic channel within therapy pad 101. If the internal fluidic channel is constructed from an expandable material, the channel would expand with pressure and the effect would be to deliver pressure to a wrapped body portion 102, via a hydraulic pressurized cuff.

Therapy Control Unit 103 further may include a sensor interface module 113, which may be used to monitor the application of stimulus to therapy pad 101. For example, if temperature-controlled stimulus is being provided to therapy pad 101, then sensor interface module 113 may measure one or both of: a temperature of therapy pad 101 and a temperature of a patient's body portion 102.

In some embodiments, pressure-controlled stimulus is provided via the therapy pad 101. Pressure controlled stimulus may include compression force on a body portion 102 resulting from hydraulic force within the therapy pad 101. Sensors 111 in communication with a sensor interface module 113 may quantify an internal pressure of therapy pad 101 as a digital or analog value, and a logical feedback loop in control module 104 may control pumps 109 and valves 108 to provide for a correct level of hydraulic pressure within the therapy pad 102 to apply a corresponding correct amount of compression to the body portion 102.

In some embodiments, a pressure transducer 110 may determine an amount of pressure against a body portion 102 and a hydraulic or fluidic pressure may be adjusted to bring the amount of pressure against the body portion 102 in compliance with a prescribed protocol.

The feedback loop for applying compressive force against the body part 102 and a surface temperature of the body part 102 may be created to periodically or continually (no artificial delay) monitor conditions experienced by the body portion 102. The therapy control unit 103 may adjust pressure and/or temperature provided by the Therapy Control Unit 103 to the therapy pad 101 and thereby control conditions experienced by body portion 102 such that conditions experienced by the body part will be in compliance with a prescribed therapy protocol comprising thermal and pressure treatments for the body portion 102.

In some embodiments, temperature and/or pressure sensors 111 may be embedded within temperature therapy pad 101 in order to generate data quantifying physical conditions experienced by the body portion 102. The sensor 111 data may be accessed by the control module 104 for feedback loops that executable software references to generate control commands By way of non-limiting example, control commands may include one or both of digital and analog electrical currents. Conditions quantified by the sensors 111 may be stored in a memory and referenced for reporting of temperature and pressure conditions experienced during a treatment session.

In some embodiments, a liner 112, such as a sleeve (or other shape) may include one or more sensors 111. The liner 112 may be positioned under a therapeutic wrap 102 in order to take measurements closer to the skin. In some embodiments, a liner 112 may be held in place with a removable attachment device, such as hook and loop, adhesive, snaps, buttons, and the like. Sensors or their liners 112 may be used with a thermal contrast therapy system 100, and may be retrofitted to existing units. Sensors 111 may integrate a feedback loop to control a specific device, e.g., a temperature sensor may be used to control a heater. Some embodiments, include a liner 112 that is not limited to a particular wrap type such that the liner 112 may be used with a variety of thermal contrast therapy systems 100 and liners 112. Feedback in the form of data provided by the liner 112 and the sensors 111 may be used to generate control commands for components of the therapy control system 100, such as pumps 109, valves 108, thermoelectric units, heaters and chillers.

Some embodiments incudes sensors 111 and/or liners 112 that are disposable. Disposability helps ensure that the sensors 111 and/or their liners 112 are sterile or at least clean of biological traces of a previous usage. Sensors 111 and/or their liners 112 may also be designed to help guard the relatively more expensive wrap from direct exposure or contact with biological tissue thus limiting transference of an adverse condition from a first patient to a second patient via use of the wrap.

Sensors 111 and/or their liners 112 may include a unique ID (e.g., a barcode, a hash code, an RFID code, etc.) associated with the patient and/or treatment. Sensors or their liners 112 may include removable storage for the generated data, and may include a wireless communication interface (e.g., Bluetooth, Near Field Communications) to a user device for data transfer.

Therapy Control Unit 103 further may include a controller 105 (see FIG. 3) or other device with a digital processor to execute a control program stored within a memory (not illustrated in FIG. 1) coupled to controller 105. For example, controller 105 may be programmed to provide a temperature-controlled therapy to therapy pad 101, according to a predetermined time versus temperature profile. The predetermined profile may be selected based upon an expected therapeutic benefit. In this example, controller 105 dynamically may control physical control module 104 to provide a fluid at a controlled temperature to therapy pad 101, and a measured feedback temperature may be received by sensor interface module 113 via data conduit 109. Controller 105 may also adjust control module 104 in order to minimize a deviation of measured feedback temperature and/or pressure to correlate with a predetermined time and treatment profile.

A predetermined time versus a treatment profile may include control over one or more of: the number of cycles between hot and cold temperatures; a hot temperature; a cold temperature; a time spent at hot temperature; a time spent at cold temperature; a transition time and/or rate between hot and cold; a shape of cyclical transitions (e.g., like a sinusoid or like a square wave); relative ratios between hot and cold; flow rates (e.g., milliliters per second) of hot and cold; and so forth. In some embodiments, a predetermined time versus temperature profile may include only cycles of heating, or only cycles of cooling.

Fluid lines 106, 107 and/or data conduit may include electrical or light based data conductors to control elements within therapy pad 101, as discussed below in further detail in connection with FIG. 2.

Therapy pad 101 may be constructed from a flexible material that can conform at least partially to a body shape, e.g., by being wrapped around a limb or to fit snugly on a scalp. However, therapy pad 101 also may include a minimum level of stiffness in order to prevent pinching of internal fluidic channels. Therapy pad 101 may include a protective outer layer in order to protect internal fluidic channels from puncture damage or the like. Therapy pad 101 also may include an outer surface texture or material that is comfortable (or at least not uncomfortable) to human touch. The outer layer also should have high thermal transmissibility.

Figure 2:
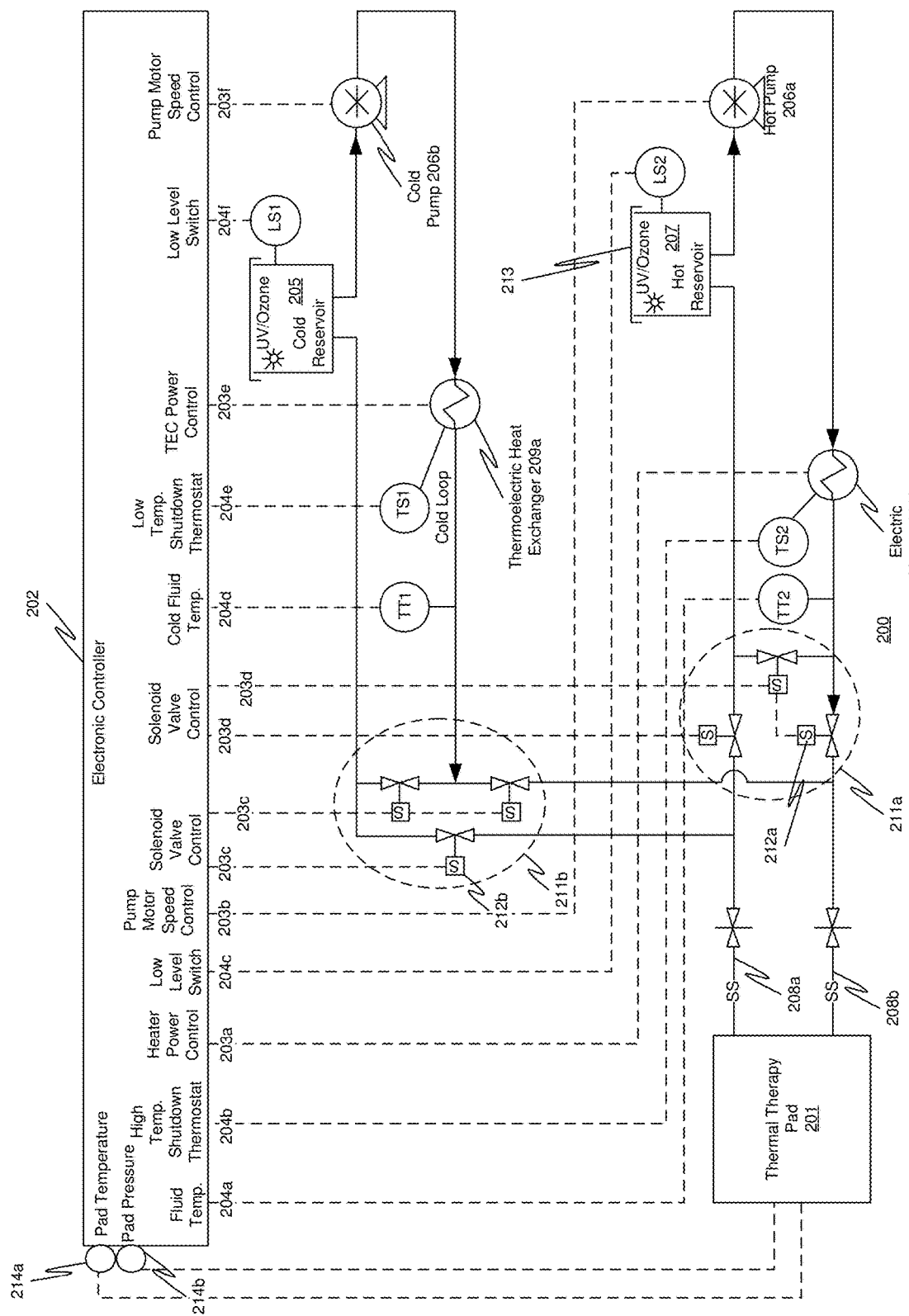
FIG. 2 illustrates at a relatively lower level of abstraction a thermal contrast therapy system according to some exemplary embodiments of the present invention.

FIG. 2 illustrates at a relatively lower level of abstraction a Thermal Contrast Therapy System 200 to administer heating, cooling, and/or pressure therapy in accordance with some embodiment of the present disclosure. Components of Thermal Contrast Therapy System 200 are interconnected as shown in FIG. 2. Thermal Contrast Therapy System 200 includes electronic controller 202, which may correspond functionally to Therapy Control Unit 103 of FIG. 1. Thermal Contrast Therapy System 200 also may include thermal therapy pad 201 (similar to therapy pad 101 of FIG. 1), a plurality of telemetric sensing or monitoring devices 204a . . . 204f (collectively, monitoring devices 204), and a plurality of control devices 203a . . . 203f (collectively, control devices 203). An individual but nonspecific monitoring device or control device may be referred to as a monitoring device 204 or a control device 203, respectively. FIG. 2 omits certain well-known features such as AC and/or DC power distribution.

A pair of fluidic lines 208a, 208b (collectively, fluidic lines 208) couple thermal therapy pad 201 to other components of Thermal Contrast Therapy System 200. One of fluidic lines 208a, 208b may be an input line, and the other of fluidic lines 208a, 208b may be an output line. Fluidic lines 208a, 208b may be flexible and have a length of up to several feet, in order for thermal therapy pad 201 to be located a short distance from the other components of Thermal Contrast Therapy System 200. For example, the other components of Thermal Contrast Therapy System 200 may be carried by a person (e.g., on a belt, in a backpack, in a "fanny pack", etc.), or be located a short distance away (e.g., on a table or equipment cart within about 5 feet of the person), while still allowing thermal therapy pad 201 to be positioned substantially anywhere on the person.

In some embodiments, Thermal Contrast Therapy System 200 may be operable either from an AC line voltage or from a direct current power source, such as a battery power. A target minimum operating time on battery power is preferably one hour.

Thermal Contrast Therapy System 200 further may include a hot fluidic line 209a, 209b (including its return, collectively hot fluidic lines 209) and a cold fluidic line 210a, 210b (including its return, collectively cold fluidic lines 210). A set of valves 211a may be used to control whether or not hot fluidic lines 209 are operationally coupled to fluidic lines 208. A similar set of valves 211b may control whether or not cold fluidic lines 210 are operationally coupled to fluidic lines 208. Hot fluidic lines 209 couple together hot fluid reservoir 207 and hot pump 206a. Cold fluidic lines 210 couple together cold fluid reservoir 205 and hot pump 206a.

Thermal Contrast Therapy System 200 further may include electronic controller 202. Electronic controller 202 may include several telemetric monitoring devices 204a . . . 204f (collectively, monitoring devices 204). Examples of monitoring devices 204 include temperature measurements of temperature sensitive or controlled elements such as fluidic lines 209, 210, thermoelectric ("TEC") heat exchangers 209a, 209b, and levels of reservoirs 205, 207.

Based upon a desired stimulus profile and measurements from monitoring devices 204, electronic controller 202 may provide control devices 203a . . . 203f (collectively, control devices 203) to the remainder of Thermal Contrast Therapy System 200, in order to provide a desired stimulus to thermal therapy pad 201. Examples of control devices 203 include valve controls 203c, 203d, power control 203a, 203e and pump controls 203b, 203f.

Some exemplary embodiments include an arrangement of valves 211a-b and pumps 206a-b as described in the drawings. In particular, a specific arrangement of v valves 211a-b and pumps 206a-b to form a feedback loop maintaining temperature levels and facilitating accelerated transition of thermal fluid applied to treated area.

According to the present invention fluid control devices, including, for example, an arrangement of valves 211a-b and pumps 206a-b and fluid lines 210a-b, may be made operative to apply thermal fluid hydraulic pressure to cuff and/or wrap pressure without need for air pressure and associated pneumatic tubing. Furthermore, in some embodiments hydraulic pressure in lines 210a-b may be applied together with pneumatic pressure. Features and benefits include reduced size of the control unit, reduced noise level, cyclical compression without irritating noise, and simpler control units with no separate air channels.

In some embodiments, pressure from air or other gas may be generated within fluid lines that are not being used to provide thermally controlled fluid during a particular cycle. For example, air pressure may be provided in chilled fluid line 210b during circulation of heated fluid in a separate heated fluid lines 210a. Compressed air in a line may be used to flush cold fluid out of the line and may additionally provide compressive pressure of the wrap around a treated body part. Alternatively, air pressure may be used to flush hot fluid out of a heated fluid line 210a. In this manner air may flush a first fluid prior to circulation of a second fluid. Still further, in some embodiments, an antimicrobial or disinfecting or cleansing solution and/or gas may also be circulated in a chilled fluid line 210b or a heated fluid line 210a when not being used to convey thermally controlled fluid. Note: this would require two separate sets of fluid lines in the pad, not shown anywhere.

Embodiments in accordance with the present disclosure may control Thermal Contrast Therapy System 100 and/or Thermal Contrast Therapy System 200 to provide a prescribed or desired therapy, including a controlled variation over time of the therapy. For example, prescribed variations of therapy may include at least one heated fluid line (e.g., hot fluidic lines 210a) and one chilled fluid line (e.g., cold fluidic line 210b), which together may provide sequentially alternating hot and cold therapy to thermal therapy pad 201 via alternating supply from fluid lines 210a and 210b via control valves 211a and 211b respectively. Some embodiments may provide additional temperature controlled loops and/or an unequal number of temperature controlled loops, such as two or more chilled fluid loops, two or more heated fluid loops, and so forth.

The present invention provides for thermally controlled fluid stored in a hot fluid reservoir 207 and cold fluid reservoir 205 is an improvement over the previous systems that are based upon a single shared reservoir to supply fluid that in turn is either heated or cooled. An equilibrium temperature of the single shared reservoir in the '614 patent will be near the center of the temperature difference between hot fluid and cold fluid weighted by the ratio of hot versus cold fluid used. In contrast, separate reservoirs included in the present application allow for a heated fluid reservoir 207 and chilled fluid reservoir 205 to maintain respective separate equilibrium temperatures, each respective equilibrium temperature is maintained closer to a respective temperature of hot or cold fluid when applied as therapy in thermal therapy pad 201. This means that less heating by thermal electric unit 209a or cooling by thermal electric unit 209b is required of the fluids drawn from hot fluid reservoir 207 or cold fluid reservoir 205. Accordingly, fewer joules of heat need to be added to hot fluid, or joules of heat removed from cold fluid. In turn, this means that TEUs 209a, 209b may have attributes that allow them to be one or more of: smaller, less costly, draw less electrical power, and/or operate more quickly to bring fluid temperature to a required therapy temperature for thermal therapy pad 201, compared to usage of a single shared fluid reservoir in the background art.

Another advantage of the present invention includes switching of a set of hot valves 211a and a set of cold valves 211b may be sequenced and/or timed in a process that can control a flow and/or volume of thermal control fluid in a loop during use and while not being used during a specified period of time.

For example, when a heating, hot fluidic lines 210a is active and a flow of fluid in cold line 210b is reduced. This provides several benefits compared to a single reservoir system of the background art. For example, unlike the background art, energy is not wasted by the thermal conditions in the respective loops not competing with each other. During a heat cycle valves may dictate that only heat is circulated through a thermal pad, and during a cooling cycle, only cool fluid is circulated through the thermal pad. In addition, in an ancillary aspect, repeatedly heating and cooling the valves themselves and the walls of dedicated lines 209b, 210b may be minimized via control of the valves. The temperature of fluid delivered to thermal therapy pad 201 can be changed more quickly since there is less hot fluid needing to be cleared from the lines when cold therapy is now desired, and less cold fluid needing to be cleared from the lines when hot therapy is now desired. For example, the temperature of fluid delivered to temperature therapy pad 201 may be changed, full range or near-full range, from a hot temperature to a cold temperature within 10-25 seconds (or less with a high speed pump).

Embodiments in accordance with the present disclosure may include a manifold controlled by solenoid valves 211a-211b, in order to connect one or more thermal therapy pads 201 to fluid lines 210a-b. The solenoid valves 211a-211b may be operated to provide rapid switching between hot and cold fluids. In some embodiments, a valve timing sequence may be provided such that a return valve is closed later. The solenoids 212a and 212b may be provided in different configurations, such as six two-way solenoids, or two three-way and two two-way solenoids, and so forth.

In some embodiments, separate pumps 206a, 206b may be associated with each respective fluidic thermal lines 210a, 210b. Separate pumps 206a, 206b may be useful to activate and to control more precisely the circulation of the temperature-controlled fluid (e.g., if placed before valves 211a, 211b to control the combination of the fluid lines). Separate pumps 206a, 206b and appropriate valve configuration also allow each of fluidic thermal lines 210a, 210b to circulate independently of each other, without entering thermal therapy pad 201, in order to better keep fluid in the respective reservoirs 205, 207 at the respective desired temperatures. In other embodiments, a single pump 206a, 206b may be provided after the valves 211a, 211b combining the hot and cold fluidic lines 210a, 210b. A single pump 206a, 206b configuration may be smaller, lighter, and less costly, but may require more complicated valving in order to alternate maintenance of temperatures of reservoirs 205, 207.

Another advantage of the present application compared to the background art is that pumps 206a, 206b may be used to increase pressure in fluidic lines 210a, 210b in order to deliver hydraulic pressure to thermal therapy pad 201 through connecting hoses 208a and 208b. The hydraulic pressure may then cause thermal therapy pad 201 to expand and provide pressure against body portion 102. In such embodiments, elements providing pressure also are delivering thermal therapy, thus offering a possibility of more efficient transfer of heat or cold to body portion 102 by the combination of pressure and direct contact by the fluid-bearing elements within thermal therapy pad 201. In contrast, for the background art that uses air and an air compressor to inflate a cuff around a body part, such pneumatic methods do not necessarily provide an equivalent level of direct contact by the fluid-bearing elements within a thermal therapy pad 201.

Another advantage of the present application compared to previously known systems, is that usage of separate pumps 206a, 206b enables less complicated application of different pressure profiles of hot fluid and cold fluid, compared to a single pump configuration. For example, if it is desired that hot therapy should be delivered with 50% higher pressure than cold therapy, then hot pump 206a simply may be set to provide 50% more pressure than cold pump 206b, and no dynamic pressure control is required for pumps 206a, 206b. In contrast, for a single pump system, pressure provided by the single pump must be dynamically controlled in coordination with the desired temperature therapy profile.

Reservoirs 205, 207 are useful to provide rapid transfer between hot and cold fluid, by helping reduce a temperature differential that the heater and/or cooler need to provide. For example, if hot and cold fluid are alternately supplied to thermal therapy pad 201, then as fluid of one temperature is supplied to thermal therapy pad 201 (e.g., hot fluid), then the fluid of the other temperature (e.g., the cold fluid) may be recirculated and placed in thermal contact with a thermal electric heat exchanger 209a to help maintain a desired temperature.

As illustrated in FIG. 2, each of fluidic lines 210a, 210b may include a respective fluid reservoir 205, 207, with fluid level sensors, which feed one or more circulating pump(s). A temperature sensor may be used to measure the respective fluid temperature of each of fluidic lines 209, 210. Fluidic lines 210a, 210b allow temperature-controlled fluid to recirculate through itself and/or flow through the therapy pad.

In some embodiments, hot fluidic line 210a may be in thermal communication with heaters (e.g., a thermoelectric 210a or resistive heater to control heated thermal fluid temperature within a range, typically ranging from about 40 degrees Celsius ("C") to about 48 degrees C. Cold fluidic thermal line 210b may be in thermal communication with a cooler (e.g., a TEC cooler) to control its fluid temperature within a range, typically ranging from about 2 degrees C. to about 12 degrees Celsius.

In some embodiments, a fluidic line 210a and 210b each may circulate thermal fluid within itself or through thermal therapy pad 201 when coupled to a person. Electronic controller 202 may modulate power separately to the heaters and coolers in order to control a respective temperature of each loop. Temperature control may be based upon a proportional-integral-derivative ("PID") control algorithm and the measured temperature of the respective fluidic line.

In some embodiments, electronic controller 202 or a secondary controller (not illustrated in FIG. 2) may control solenoid valves 211a-211b that direct the hot and cold circulating fluids either to the therapy pad or to recirculate within the loop.

In addition, cyclical compression as desired also may be provided. For example, a speed of one or more pumps 206a-206b may be varied or modulated by use of the controller (i.e., either electronic controller 202 or the secondary controller if present) to provide cyclical compression. A user or a therapy profile may specify a desired stimulus profile of hot fluidic line 209 and cold fluidic line 210. For example, electronic controller 202 may be programmed to set respective desired temperatures of hot fluidic line 210a and cold fluidic line 210b; to set respective time periods that hot fluidic line 210a and cold fluidic line 210b circulate through thermal therapy pad 201, or recirculate without entering thermal therapy pad 201, or no circulation at all; to set a number of hot/cold cycles each treatment performs; and to set a desired compression cycle at each temperature.

In some embodiments, an integrated sterilizer 213 may sterilize fluid periodically or continuously in each reservoir in order to prevent bacteria growth. The sterilizer 213 may use technology such as an ultraviolet ("UV") light source (including an UV light emitting diode ("LED")), or introduction of an ionized or reactive gas such as ozone, and so forth. The sterilizer 213 may be located in or more of the reservoirs 206, 207, and/or along fluidic lines 210a, 210b. At least a portion of reservoirs 206, 207, and/or fluidic lines 210a, 210b may be made from a UV-transmissive material in order to pass UV light for sterilization.

In some embodiments, a log or record of measured temperatures in Thermal Contrast Therapy System 200 and/or on the patient may be maintained for contemporaneous or post-treatment analysis. For example, patient temperatures may include a record of skin temperature during therapy. Temperatures measured, for example, via infrared probe, bimetal sensor or other sensor.

In some embodiments, temperature measured from a patient (e.g., the patient's measured skin temperature) may be used as feedback to adjust operating parameters of Thermal Contrast Therapy System 200. For example, if a sensor quantifying skin temperature indicates that a patient's skin temperature is too high relative to a desired therapeutic profile, operation of Thermal Contrast Therapy System 200 may be adjusted to lower the temperature of hot fluidic line 210a, or to reduce an amount of time that hot fluid is provided to thermal therapy pad 201, or to increase the amount of time that cold fluid is provided to thermal therapy pad 201, or to reduce the ratio of hot/cold operating time, and so forth, including a combination of methods.

In some embodiments, Thermal Contrast Therapy System 200 may be configured to provide an auditable record of control system operation, such as treatment time and date, patient data (e.g., measured skin temperature during treatment), therapy data (e.g., some or all of telemetric monitoring devices during treatment), compliance with a desired treatment profile, and so forth. In some embodiments, an interface to a remote web-based or cloud-based computing platform may be provided, at least to maintain the auditable record of control system operation.

In some embodiments, compression may be varied by varying a speed of pumped thermal fluid. Pumped thermal fluid speed may be varied by techniques such as: (a) controlling speed of the pump itself; (b) use of a pressure control orifice to set pressure levels; and/or (c) use of a pressure sensor to set pressure levels. At least some of these methods do not necessarily need to control speed of the pump itself. Sensors 214a-214b to measure speed and/or pressure of the pumped fluid may include a piezoelectric sensor in thermal therapy pad 201, and/or a fluid pressure sensor.

Figure 3:
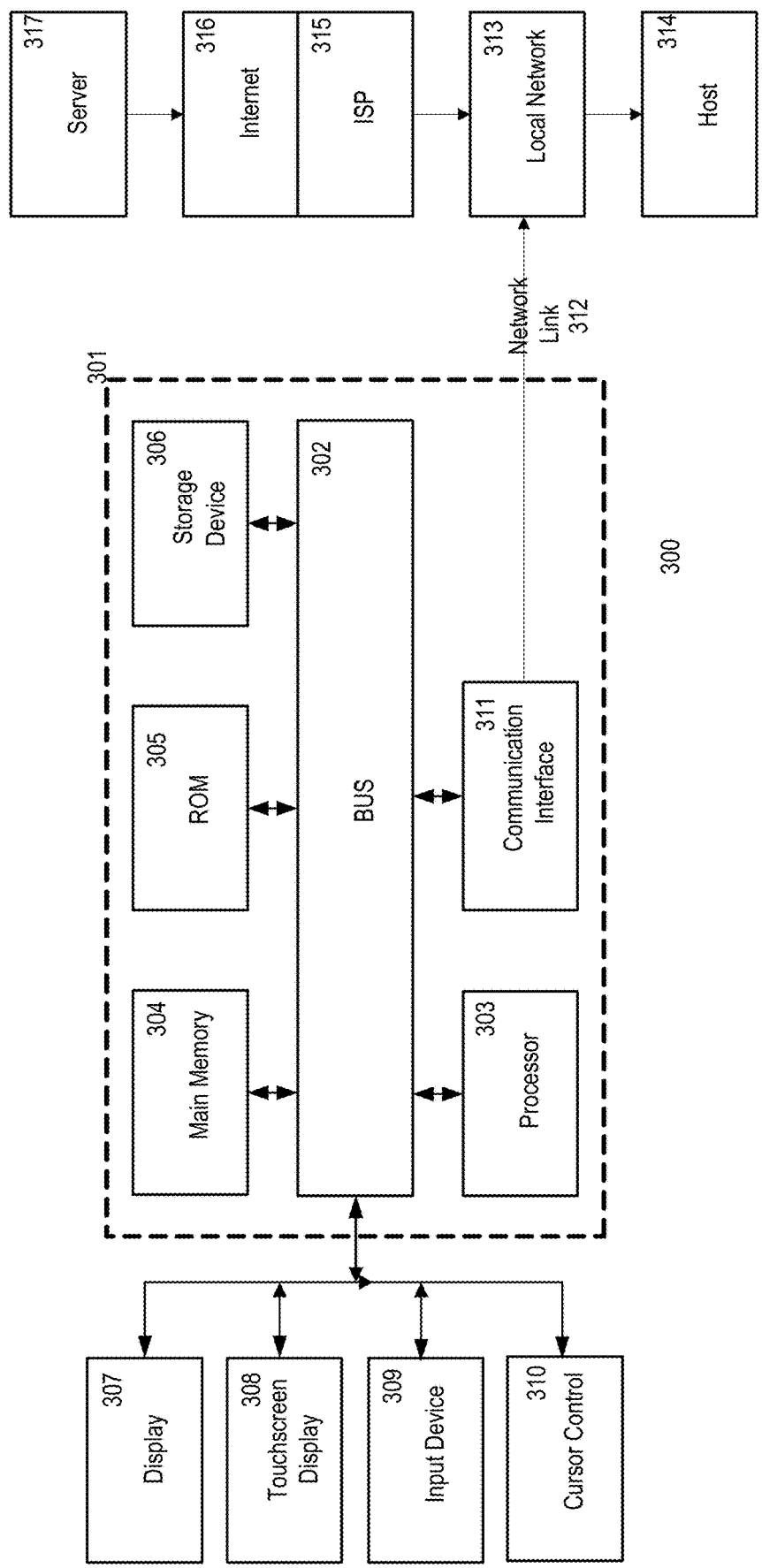
FIG. 3 illustrates a functional block diagram of a controller for a thermal contrast therapy system according to some exemplary embodiments of the present invention.

FIG. 3 illustrates a functional block diagram of a controller 300 in accordance with some embodiment of the present disclosure. Controller 301 may be useful to implement embodiments of the present invention, e.g., usable to function as at least part of electronic controller 202.

Controller 301 may include a bus 302 or other communication mechanism for communicating information, and a processor 303 coupled with bus 302 for processing information. In some embodiments, bus 302 may represent more than one individual bus, e.g., a fast bus to access fast components such as main memory 304 and Processor 303, and a separate relatively slower bus to access slower components such as user interface devices (displays 307, 308, input device 309 and cursor control 310), storage device 306, and/or communication interface 311.

Controller 301 also includes a main memory 304, such as a random access memory (RAM) or other dynamic storage device, coupled to bus 302 for storing information and instructions to be executed by microcontroller 354. Main memory 304 may also be used for storing temporary variables or other intermediate information during execution of instructions to be executed by Processor 303. Controller 301 further includes a read only memory (ROM) 305 or other static storage device 306.

Controller 301 may be coupled via bus 302 to a display 307, such as a light emitting diode (LED) display, organic light-emitting diode (OLED), projector, or heads up display for displaying information to a computer user. An input device 309, including alphanumeric and other keys, may be coupled to bus 302 for communicating information and command selections to Processor 303. Another type of user input device is cursor control 310, such as a mouse, a trackball, a touchpad, or cursor direction keys for communicating direction information and command selections to Processor 303 and for controlling cursor movement on display 307. Another type of user input device is a touchscreen display 308 where a user may communicate information and command selections to Processor 303 by tactile interaction with the display thereby controlling cursor movement or alphanumeric and other keys. This input device typically has two degrees of freedom in two axes, a first axis (e.g., x) and a second axis (e.g., y), that allows the device to specify positions in a plane.

Embodiments of the invention are related to the use of controller 301 for setting operational parameters relating to operation of thermal therapy pad 201. According to some embodiment of the invention, layering system parameters are defined and managed by controller 301 in response to Processor 303 executing one or more sequences of one or more instructions contained in main memory 304. Such instructions may be read into main memory 304 from another computer-readable medium, such as storage device 306. Execution of the sequences of instructions contained in main memory 304 causes Processor 303 to perform the process steps described herein. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to Processor 303 for execution. Such a medium may take many forms, including but not limited to, non-volatile media, volatile media, and transmission media. Non-volatile media includes, for example, a storage device 306 and ROM 305. Volatile media includes dynamic memory, such as main memory 304. Transmission media includes coaxial cables, copper wire and fiber optics, including the wires that comprise bus 302. Transmission media may also take the form of electromagnetic waves, such as those generated by Bluetooth™ or WiFi and infrared data communications.

Common forms of computer-readable media include, for example, a SSD (solid state disk), a memory stick, hard disk or any other magnetic medium, a CD-ROM, any other optical medium, a RAM, a PROM, and EEPROM, any other memory chip or cartridge, or any other medium from which a computer may read.

Various forms of computer readable media may be involved in carrying one or more sequences of one or more instructions to Processor 303 for execution. For example, the instructions may initially be carried on a magnetic disk of a remote computer. The remote computer may load the instructions into its dynamic memory and send the instructions over a distributed network such as the Internet. A communication device may receive the data on the telephone line, cable line, or fiber-optic line and use an infrared transmitter to convert the data to an infrared light pattern corresponding with a logical value. An infrared detector may receive the data carried in the infrared light pattern and appropriate circuitry may place the data on bus 302. Bus 302 carries the data to main memory 304, from which Processor 303 retrieves and executes the instructions. The instructions received by main memory 304 may optionally be stored on storage device 306 either before or after execution by Processor 303.

Controller 301 also includes a communication interface 311 coupled to bus 302. Communication interface 311 provides a two-way data communication coupling to a network link 312 that may be connected to a local network 313. For example, communication interface 311 may operate according to the internet protocol. As another example, communication interface 311 may be a local area network (LAN) card allowing a data communication connection to a compatible LAN. Wireless links may also be implemented. Network link 312 typically provides data communication through one or more networks to other data devices. For example, network link 312 provides a connection through local network 313 to a host computer 314 or to data equipment operated by an Internet Service Provider (ISP) 315. ISP 315 in turn provides data communication services through the worldwide packet data communication network now commonly referred to as the "Internet" 316. Local network 313 and Internet 316 both use electrical, electromagnetic or optical power values that carry digital data logic. The power values through the various networks and through communication interface 311, carry the digital data to and from controller 301 are exemplary forms of carrier waves transporting the information.

In some embodiments, Controller 301 may send messages and receive data, including program code, through the network(s), network link 312 and communication interface 311. In the Internet example, a server 317 might transmit a requested code for an application program through Internet 316, ISP 315, local network 313 and communication interface 311.

Processor 303 may execute the received code as it is received, and/or stored in storage device 306, or other non-volatile storage for later execution. In this manner, controller 301 may obtain application code in the form of a carrier wave.

Access devices may include any device capable of interacting with controller or other service provider. Some exemplary devices may include a mobile phone, a smart phone, a tablet, a netbook, a notebook computer, a laptop computer, a wearable computing or electronic device, a terminal, a kiosk or other type of automated apparatus. Additional exemplary devices may include any device with a microcontroller executing programmable commands to accomplish the steps described herein.

A controller may be a programmable board such as an Arduino™ or Raspberry Pi™ microprocessor board, and/or one or more of: personal computers, laptops, pad devices, mobile phone devices and workstations located locally or at remote locations, but in communication with the system. System apparatus may include digital electronic circuitry included within computer hardware, firmware, software, or in combinations thereof. Additionally, aspects of the invention may be implemented manually.

Apparatus of the invention may be implemented in a computer program product tangibly embodied in a machine-readable storage device for execution by a programmable processor and method actions may be performed by a programmable processor executing a program of instructions to perform functions of the invention by operating on input data and generating output. The present invention may be implemented advantageously in one or more computer programs that are executable on a programmable system including at least one programmable processor coupled to receive data and instructions from, and to transmit data and instructions to, a data storage system, at least one input device, and at least one output device. Each computer program may be implemented in a high-level procedural or object oriented programming language, or in assembly or machine language if desired, and in any case, the language may be a compiled or interpreted language. Suitable microcontrollers include, by way of example, a processor and memory combination.

Generally, a processor will receive instructions and data from a read-only memory and/or a random access memory. Generally, a computer will include one or more mass storage devices for storing data files; such devices include magnetic disks, such as internal hard disks and removable disks magneto-optical disks and optical disks. Storage devices suitable for tangibly embodying computer program instructions and data include all forms of non-volatile memory, including, by way of example, semiconductor memory devices, such as EEPROM and flash memory devices; magnetic disks such as, internal hard disks and removable disks; and CD ROM disks. Any of the foregoing may be supplemented by, or incorporated in, ASICs (application-specific integrated circuits).

In some embodiments, implementation of the features of the present invention is accomplished via digital computer utilizing uniquely defined controlling logic, wherein the controller includes an integrated network between and among the various participants in Process Instruments.

The specific hardware configuration used is not particularly critical, as long as the processing power is adequate in terms of memory, information updating, order execution, redemption and issuance. Any number of commercially available database engines may allow for substantial account coverage and expansion. The controlling logic may use a language and compiler consistent with that on a CPU included in the medical device. These selections will be set according to per se well-known conventions in the software community.

Figure 4:
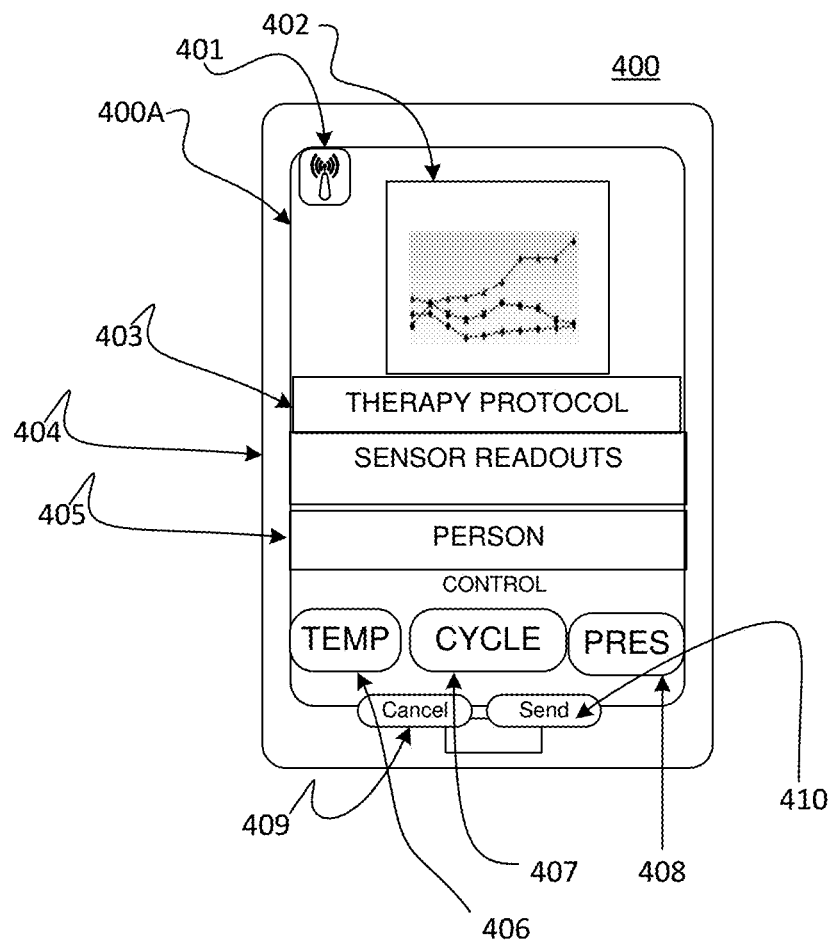
FIG. 4 illustrates a smart device and user interface according to some embodiments of the present invention.

Referring now to FIG. 4, a smart device 400 is illustrated with a human readable graphical user interface 400A. In some embodiments, a smart device 400 may be used to set parameters and protocols within a Therapy Control Unit 103 (not illustrated in FIG. 4). The smart device will typically communicate via an embedded wireless device 401 that may use a form of near field communication (such as IEEE 802.15.1 known as Bluetooth™, WiFi through a router, or IEEE 802.15.4 known as ZigBee™) to interact with the Therapy Control Unit 103. Interactive user controls on the smart device may set therapy protocols 403, process sensor readings 404; identify a patient receiving therapy 405, or other functionality. In some embodiments, data 402 may be displayed for review by one or both of: a therapy provider and a patient. The data may include, for example, sensor readings at specified time intervals.

In another aspect, a smart device 400 may include control modules that allow for wireless control of one or more protocol parameters, such as: temperature settings 406; number of cycles and length of respective cycles 407; and an amount of pressure 408 to accompany the respective cycles. In addition, a cancel control 409 may reset the smart device app and a "send" control 410 may wirelessly send one or more of: sensor readings 404, protocol parameters, date and time, location (via, for example GPS), a user identifier (such as an alphanumeric universally unique identifier UUID). The send button may communicate via a Wi-Fi, cellular network or other wireless platform.

Figure 5:
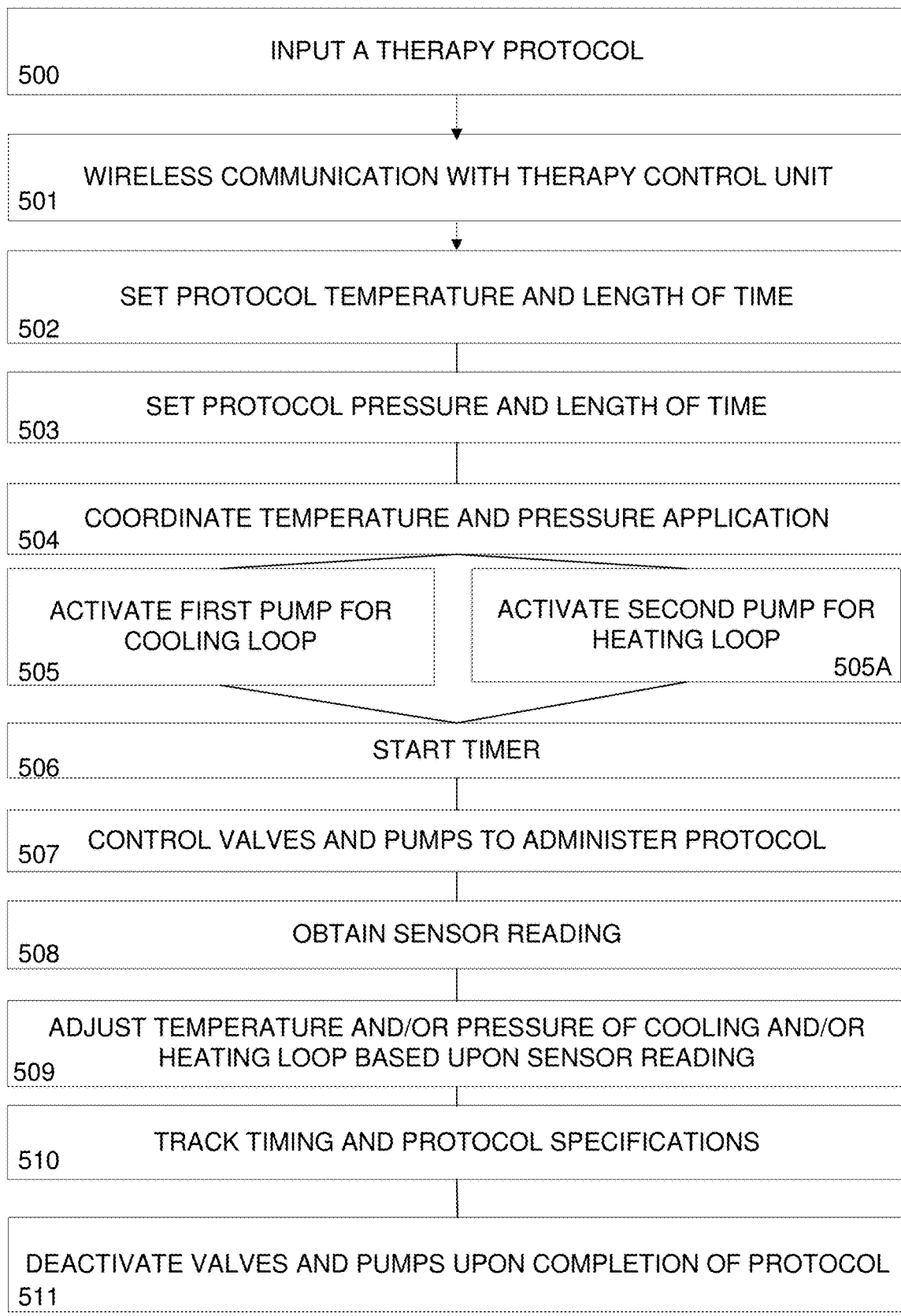
FIG. 5 illustrates method steps that may be implemented in some embodiments of the present invention.

Referring now to FIG. 5, method steps are presented that may be followed in whole or in part in various implementations of the present invention. At method step 500, a user or health care provider may input a therapy protocol. The therapy protocol may be entered into a Therapy Control Unit, or via a smart device. At method step 501, in some embodiment's a therapy protocol may be entered remotely and transmitted to a Therapy Control Unit digital transmission, such as via wireless communication, Bluetooth, a network, such as one or more of: the Internet, via a cellular or wireless network and via near field communications.

At method step 502, a protocol temperature and length of time may be input. At method step 503, a protocol pressure and length of time may be set.

At method step 504, a temperature and pressure specified for a protocol may be coordinated. Coordination may include, for example, an amount of pressure that will be applied while an amount of heat or cooling therapy is simultaneously applied.

At method step 505 a first pump may be activated to control circulation of a cooling fluid. At method step 505A a second pump may be activated to control circulation of a heating fluid. One or both of method steps 505, 505A may be performed, either in sequence, or at least partially concurrently, or individually without the other of method steps 505, 505A. At method step 506 a timer may be started to associate a time that a protocol step or cycle is administered and at method step 507 one or more valves and pumps may be controlled to administer the therapy protocol input.

At method step 508, the Therapy Control Unit may receive one or more sensor readings and at method step 509 the Therapy Control Unit may adjust one or both of the cooling and heating loop based upon the sensor readings received.

At method step 510, timing of one or both of a heating cycle and a cooling cycle and an amount of pressure applied during the respective cycles may be tracked in accordance with the protocol specifications.

At method 511, one or both of valves and pumps may be deactivated upon completion of the therapy protocol. Other method steps may be included and variations of those steps described above are all within the scope of the present invention.

Figure 6:
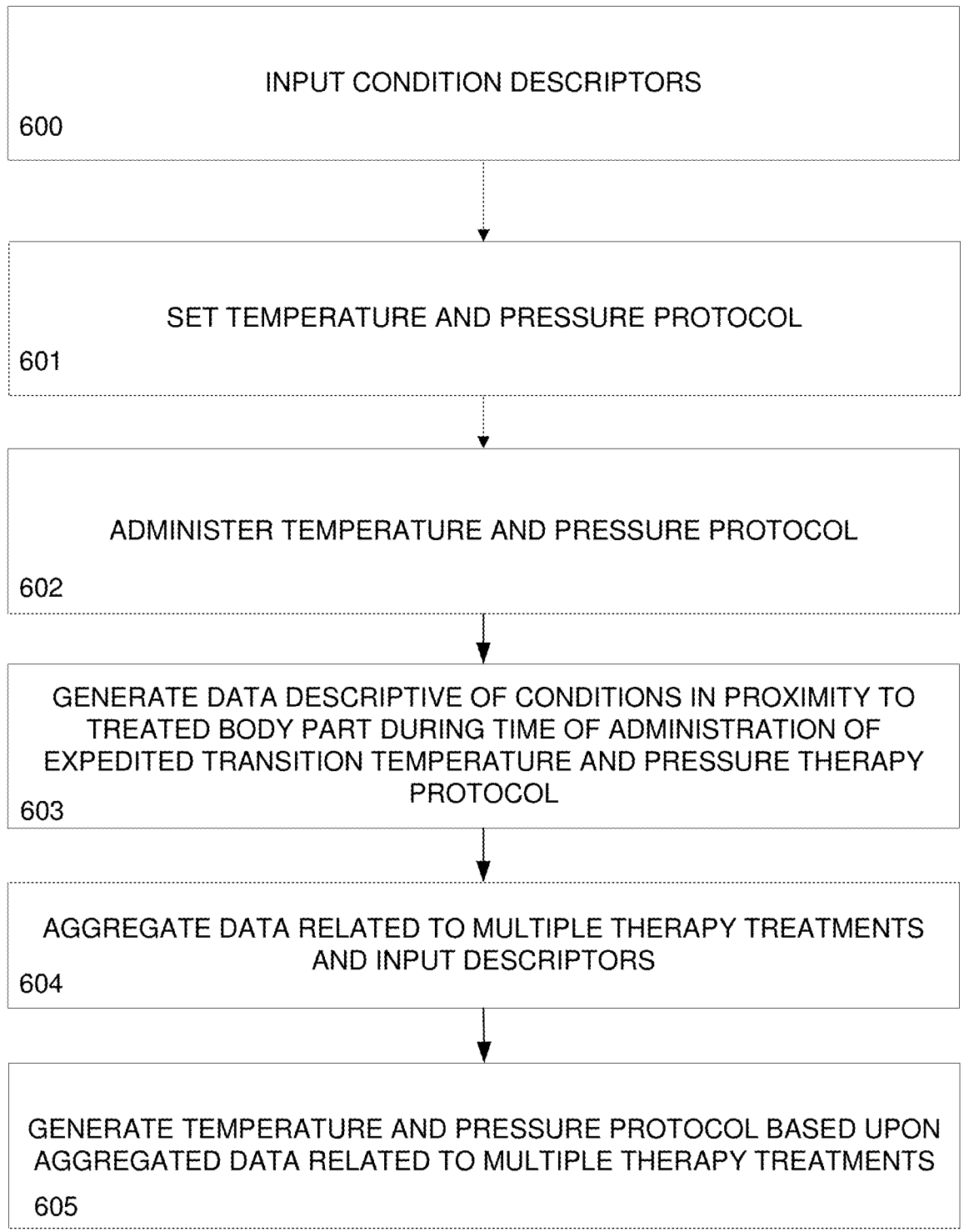
FIG. 6 illustrates additional method steps that may be implemented in some embodiments of the present invention.

Referring now to FIG. 6, additional method steps are listed that relate to aggregation of therapy treatment data and generation of therapy protocols based upon the aggregated data. At method step 600 a user or health care practitioner or therapy practitioner may input condition descriptors and at method step 601 set a temperature and a pressure protocol for a patient to receive. At method step 602 a patient may be administered a temperature and pressure protocol.

At method step 603 data that is descriptive of conditions in proximity to a treated body part during a time of administration of an expedited transition temperature and pressure therapy protocol.

At method step 604, data generated during the administration of the expedited transition temperature and pressure therapy is aggregated. In some preferred embodiments the data may be aggregated across multiple treatments including one or multiple patients.

At method step 605, a new, fast transition temperature and pressure protocol may be generated based upon the aggregated data and success patterns for treatments.

Figure 7:
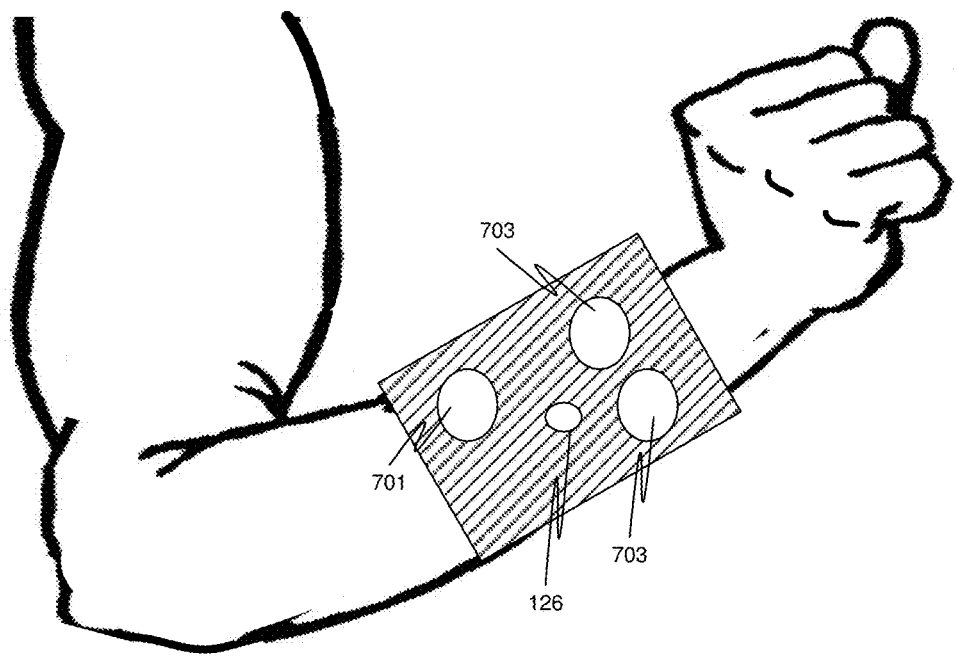
FIG. 7 illustrates a thermal contrast therapy pad according to an exemplary embodiment.

FIG. 7 illustrates an alternative embodiment 700 of a temperature therapy pad 701. In particular, temperature therapy pad 701 is similar to temperature therapy pad 101 and/or thermal therapy pad 201, but further includes one or more integrated light therapy sources 703 (for sake of clarity, not all integrated light therapy sources are marked with a reference number in FIG. 7). Light therapy also may be known as phototherapy or heliotherapy, and may include exposure to specific wavelengths or ranges of wavelengths of light that are expected to provide a therapeutic benefit. The therapeutic benefit may include a proven clinical effect and/or a placebo benefit. The light may be administered for a prescribed amount of time and/or time of day (e.g., at night during sleep). Embodiments in accordance with the present disclosure combine light therapy with accelerated transition thermal contrast therapy in order to provide a more com-pact device 701 that is able to deliver both types of therapy to the same body part, and deliver the therapies simultaneously if desired.

Temperature therapy pad 701 includes one or more integrated light therapy sources 703 that deliver the therapeutic light. Light therapy sources 703 are positioned in order to emit light toward a body part when temperature therapy pad 701 is attached to the body part. Temperature therapy pad 701 may differ from the depiction of FIG. 7, e.g., by usage of a different number of light therapy sources 703 or different placement of light therapy sources 703. In some embodiments, light therapy sources 703 may be dynamically controlled to provide light that varies over time in intensity, wavelength, or other characteristic. The light therapy may be combined with temperature and pressure therapy, either sequentially or at least partially at the same time.

In some embodiments, operation of the light therapy sources 703 may be coordinated with delivery of temperature and/or pressure therapy by temperature therapy pad 701. As such, one or more light therapy sources 703 may emit light either: a) independent of a temperature condition associate with the wrap; b) independent of a pressure condition associated with the wrap; c) in combination with a specific light therapy state; d) in combination with a specific pressure state and in combination with both temperature and pressure state caused b, or otherwise associated with the wrap.

Figure 8:
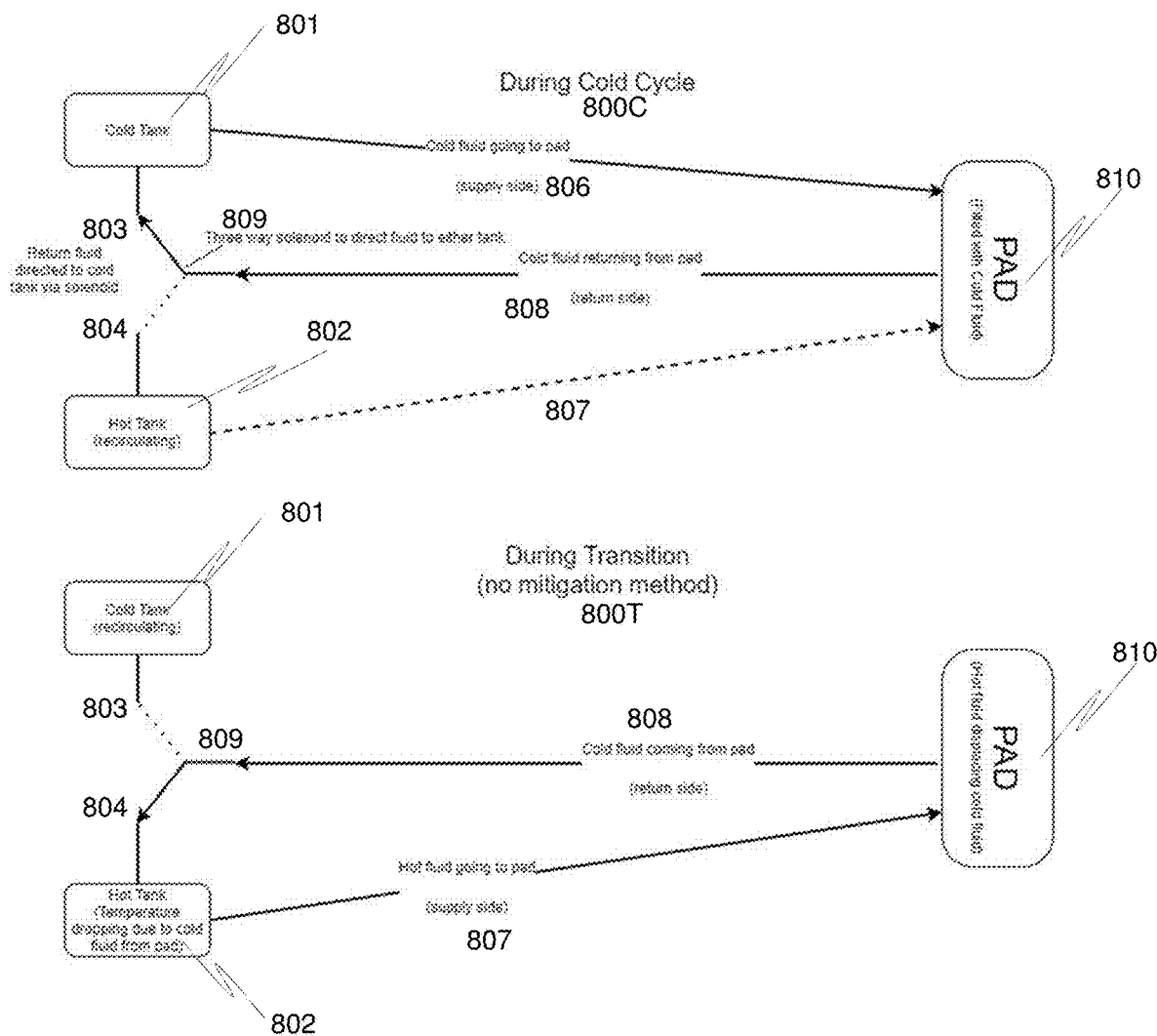
FIG. 8 illustrates a fluid circulation path in a thermal therapy system according to the present invention during a cold state and during transition with no mitigation mechanism.

Referring now to FIG. 8, a block diagram illustrates a contrast therapy pad 800 in thermal communication with a Cold Tank 801 and a Hot Tank 802 via supply thermal fluid lines 806-807 and return fluid line 809. A valve 809 (such as, for example, a threeway valve) is operative to toggle a flow of thermal fluid from return thermal fluid line 808 into either a cold tank return line 803 leading into a cold tank 801 or a hot tank return line 804 leading into a hot tank 802. During the cold cycle 800C, the valve 809 directs the flow of thermal fluid returning from the thermal therapy pad 810 into the cold tank return line 803 leading into cold tank 801. During transition 800T, the valve 809 switches the flow of thermal fluid returning from the thermal therapy pad 810 into the hot tank return line 804 leading into a hot tank 802 with no artificial delay in flow of the thermal fluid.

Figure 10:
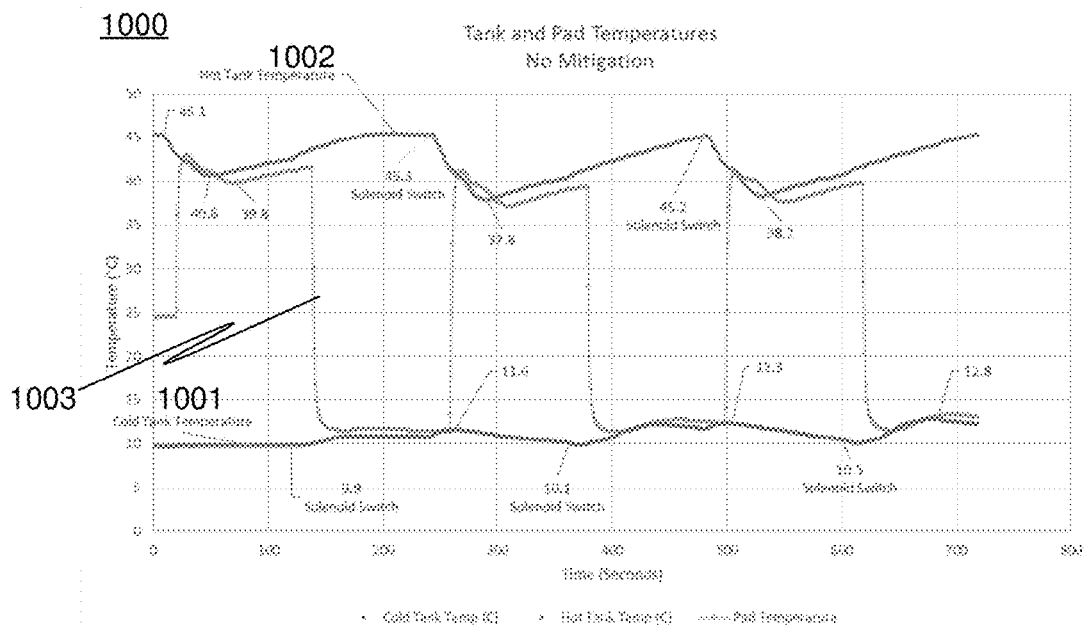
FIG. 10 illustrates a graph of temperatures present in a fluid storage tank and a thermal therapy pad during a thermal contrast cycle without the mitigation processes presented herein being utilized.

The graph illustrated in FIG. 10 quantifies a hot tank temperature 1002 that dips as the return flow of thermal fluid is transitioned from returning to the cold tank 801 into the hot tank 802. At approximately time 0 to 10 seconds the hot tank temperature 1002 is approximately 45.1° C. (hot tank set temperature) to approximately 40.6° C. from time ("T")=10 seconds to T=50 seconds. The hot tank temperature 1002 does not return to hot tank set temperature of 45° C. until after a hot cycle for supply of heated thermal fluid to the thermal pad 800 is complete and almost halfway through the cold cycle (T=200 seconds). With no mitigation, the hot tank had a temperature of less than the hot tank set temperature 45° C. during the entire hot cycle (approximately T=25 seconds to T=130 seconds). Two additional hot cycles (beginning at T=280 seconds and T=500 seconds) shown on the graph indicate a similar result.

Figure 8A:
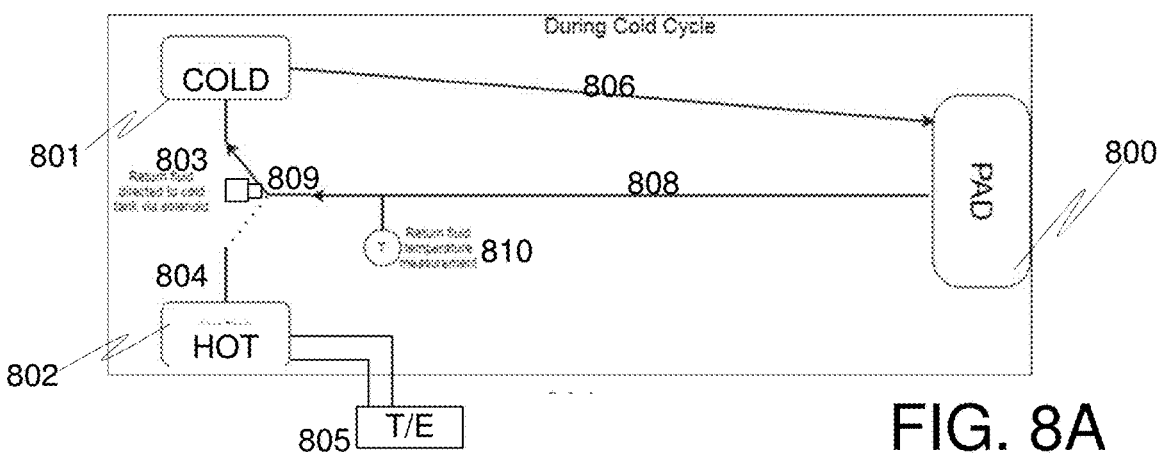
FIGS. 8A-8D illustrate exemplary states of fluid circulation in a thermal therapy system according to the present invention through paths a temperature therapy wrap pad.
Figure 8B:
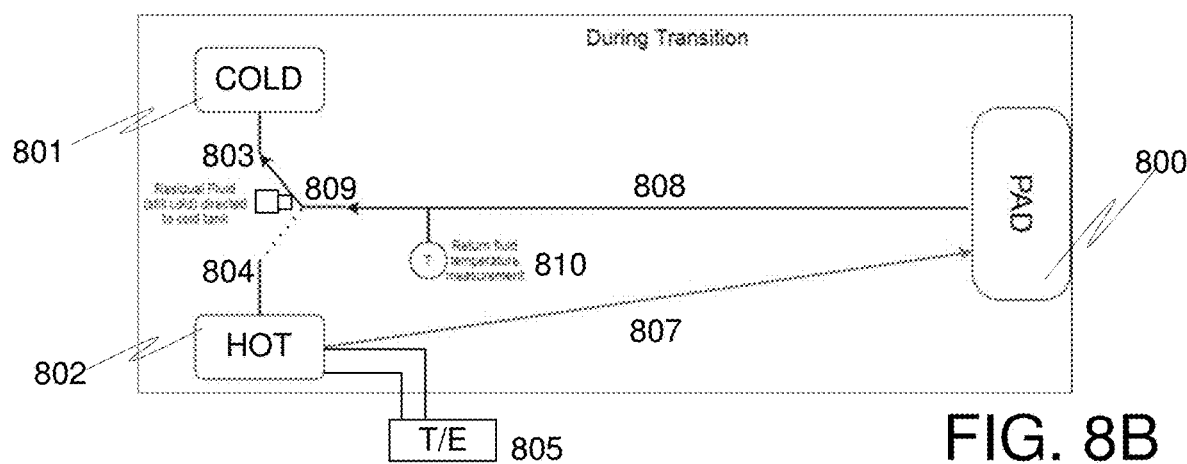
Figure 8C:
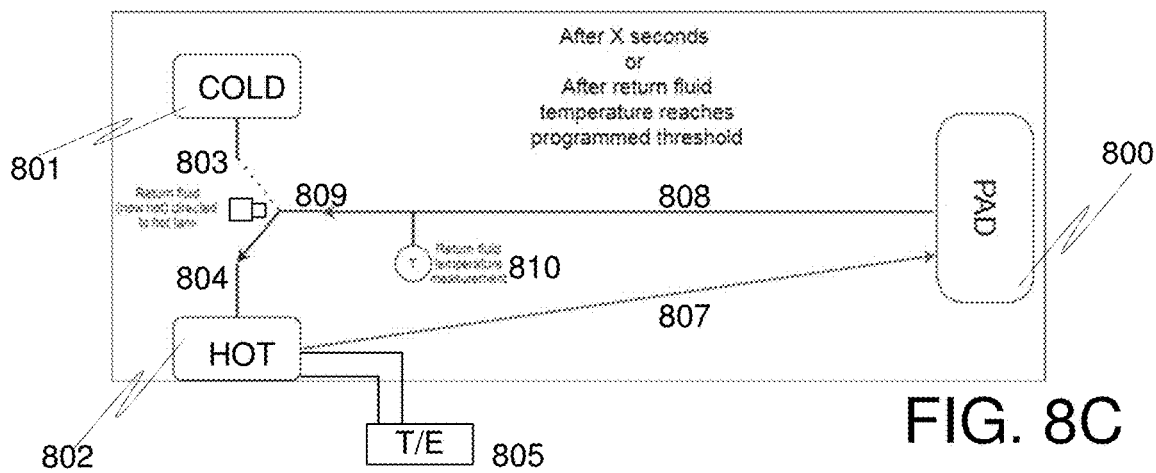

Referring now to FIGS. 8A-8C, block diagrams illustrate circulation of heated or chilled thermal fluid through a temperature therapy pad 800 and returned to either a cold tank return line 803 leading into a Cold Tank 801 fluid reservoir or a hot tank return line 804 leading into a Hot Tank 802 fluid reservoir.

As illustrated in FIG. 8A, during a temperature cycle circulating chilled thermal fluid through a temperature therapy pad 800 (Cold Cycle), the solenoid 809 directs fluid returning from the temperature therapy pad 800 (return fluid) to a Cold Tank 801 fluid reservoir. The Hot Tank 802 contains fluid that is kept at a raised temperature level (as compared to a temperature in the Cold Tank 801). The temperature level of one or both of the hot thermal fluid and cold thermal fluid may be set and maintained via one or more thermoelectric temperature control units 805 (sometimes referred to as a TEC). A temperature of one or more of the return fluid, fluid in the Cold Tank 801 and fluid in the Hot Tank 802 may be measured via a temperature sensor 803.

FIGS. 8B-8C, illustrates a transition period during which a Cold Cycle is transitioned to a Hot Cycle. The transition period includes a period of time to cycle a first thermal fluid, (in this example a chilled thermal fluid) out of the thermal therapy pad 800 and replace the thermal fluid in the thermal therapy pad 801 with a second thermal fluid (in this example a heated thermal fluid) such that the heated thermal fluid is directed to flow through the temperature therapy pad 800 for a predetermined period of time (Hot Cycle).

During a transition period from a Cold Cycle to a Hot Cycle, Hot Fluid is supplied into the Thermal Therapy Pad 800 from the Hot Tank 802. A temperature of a return fluid from the Thermal Therapy Pad 800 may be measured via the temperature sensor 810. If the temperature measurement is below a threshold temperature specification, the return fluid is directed via actuation of a solenoid 809 to the Cold Tank 801. As the return thermal fluid rises to a threshold Hot Cycle temperature, the return thermal fluid is directed via activation of the valve 809 back to the Hot Tank 802.

During a transition period from a Hot Cycle to a Cold Cycle, a process is completed wherein Cold Thermal Fluid is supplied into the Thermal Therapy Pad 800 from the Cold Tank 801. A temperature of a return fluid from the Thermal Therapy Pad 800 may be measured via the temperature sensor 810. If the temperature measurement is above a threshold temperature specification, the return fluid is directed via actuation of the solenoid 809 to the Hot Tank 802. As the return thermal fluid is reduced to a Cold Cycle threshold temperature, the return thermal fluid is directed via activation of the valve 809 back to the Cold Tank 801.

In preferred embodiments, thermal fluid is maintained in a respective reservoir in both the Hot Tank and the Cold Tank. The thermal fluid may be in thermal communication with a thermoelectric device 805 and brought to a controlled temperature via thermal communication with a Peltier device. In other embodiments, a heater element or other heating mechanism or a cooling compressor or other cooling device may be in thermal communication with the thermal fluid contained in the respective reservoirs. Direction of the return fluid to either of the Heated Fluid Reservoir in the Hot tank 804 and the Cold Fluid Reservoir in the Cold Tank 803 may be accomplished after a timed delay (such as, for example, 10 or more seconds) or after the return fluid reaches a programmed or predetermined threshold temperature. Predetermination may be accomplished, for example via an electronic thermocouple in logical communication with the valve 809, a mechanical thermostat actuated via a thermal spring, or other temperature actuated device.

Figure 8D:
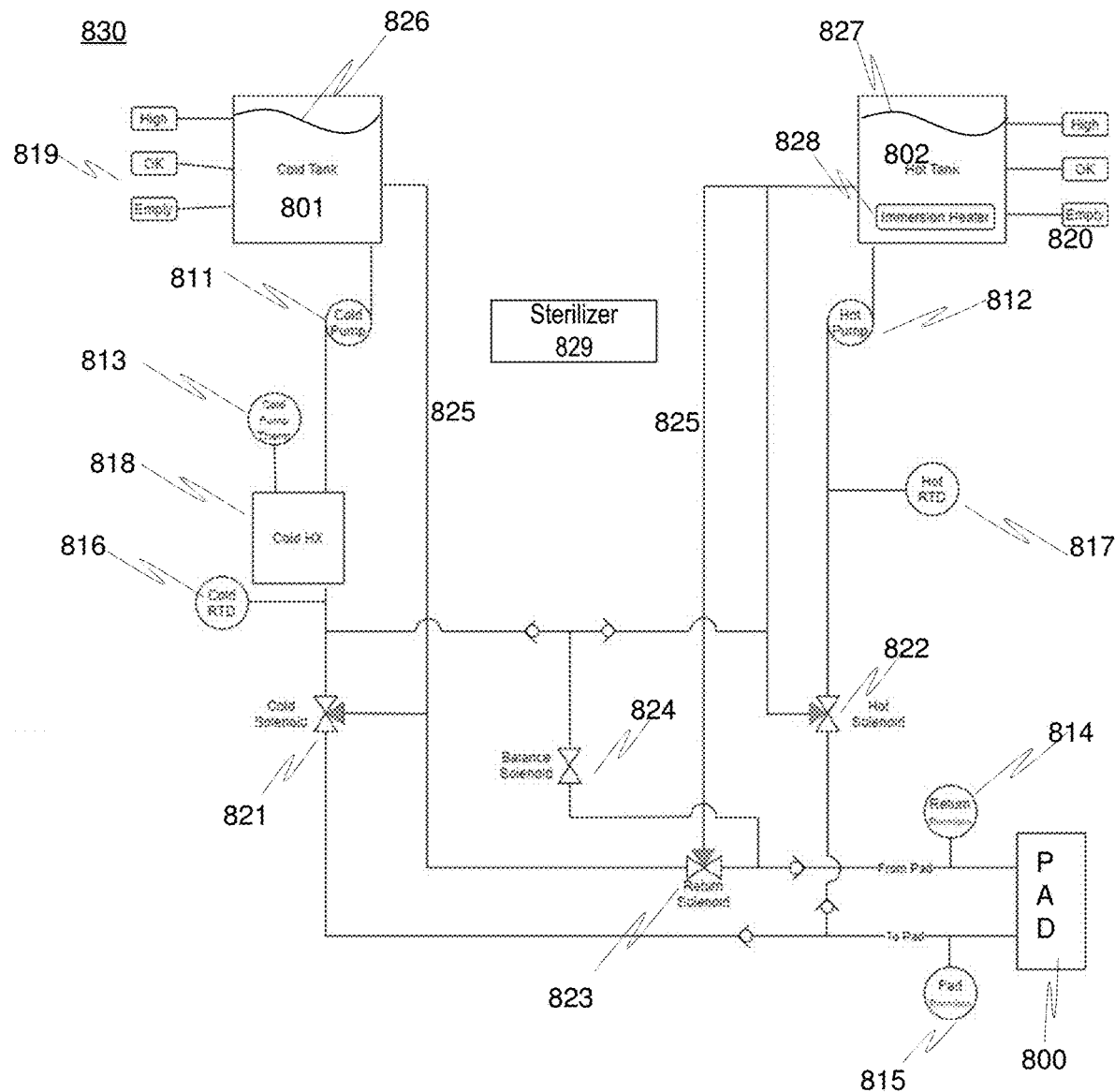
Figure 9A:
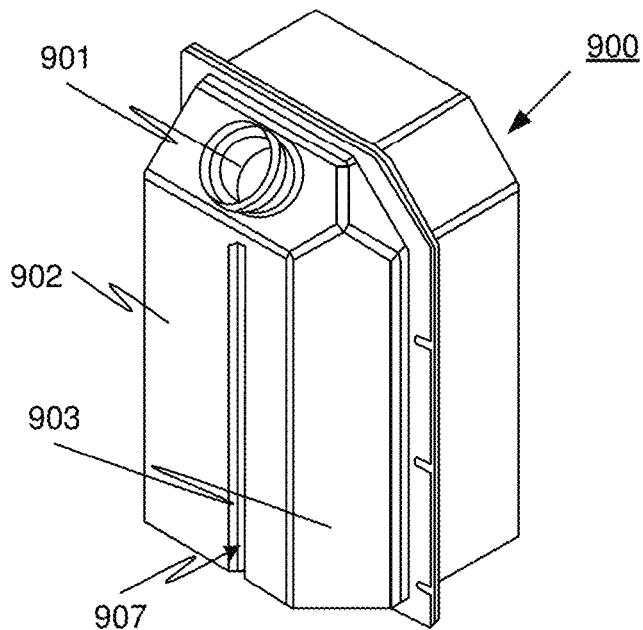
FIGS. 9A-9D illustrate various aspects of a fluid tank according to some embodiments of the present invention.
Figure 9B:
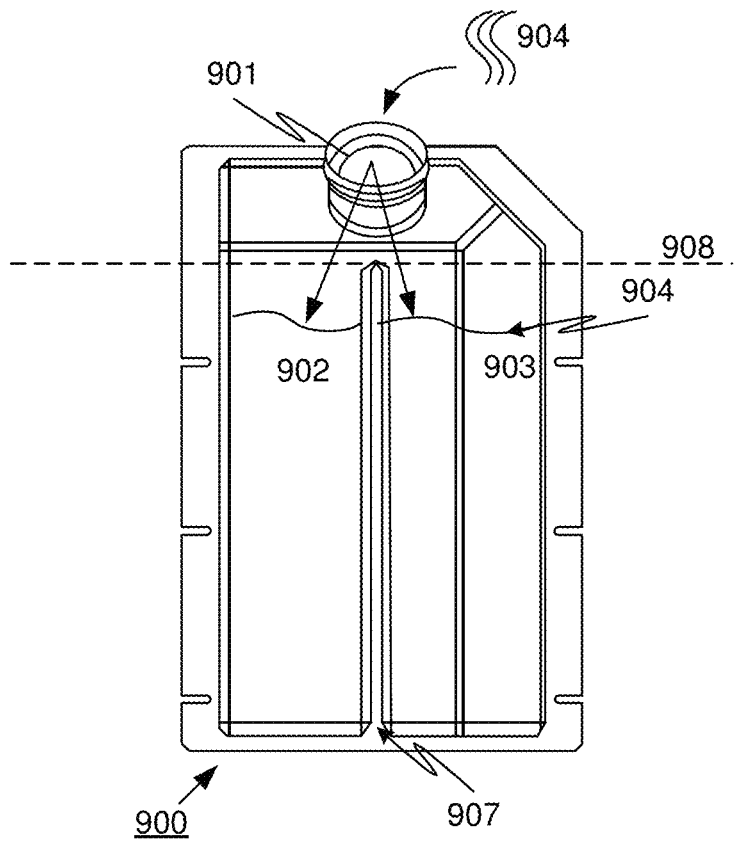
Figure 9C:
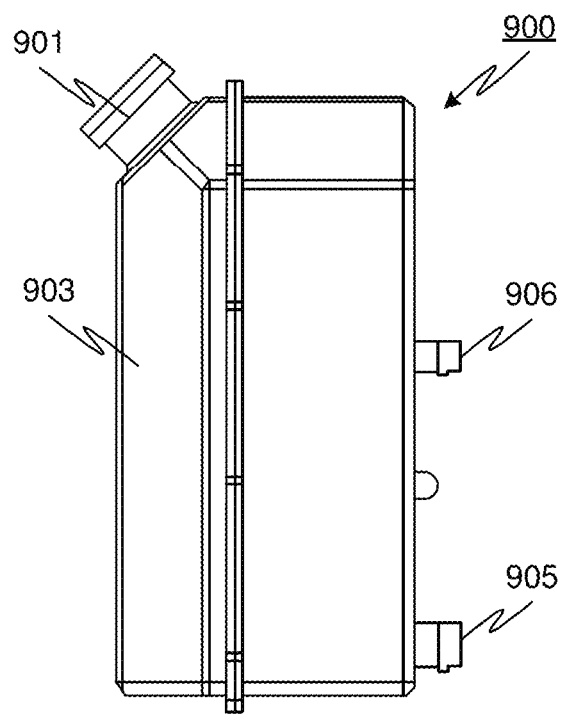
Figure 9D:
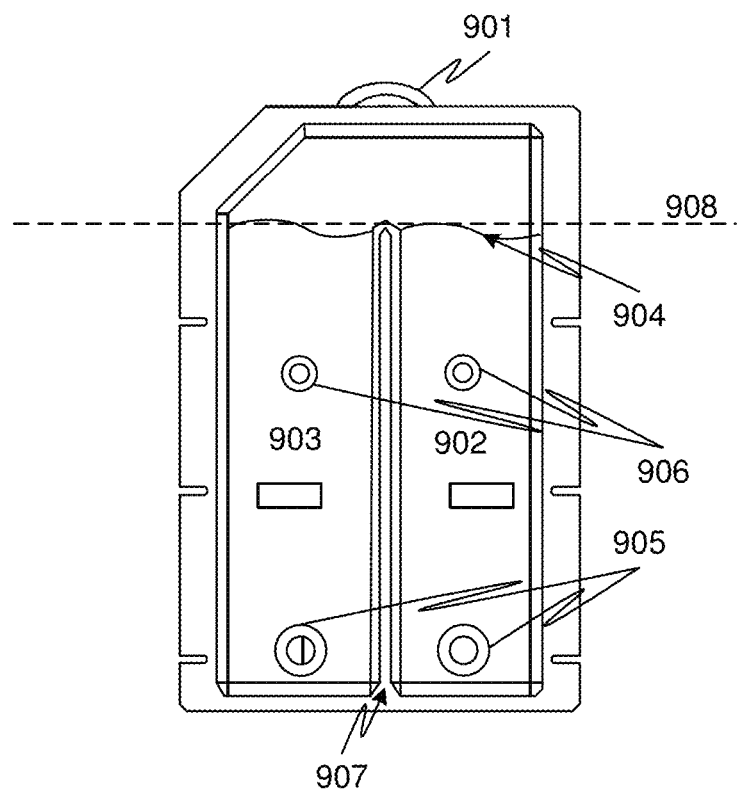

Referring now to FIG. 8D, a detailed view of exemplary embodiments of the higher level representations of FIGS. 8A-8C is illustrated. A Cold Tank 801 and a Hot Tank 802 are shown, each in fluid communication with a Thermal Therapy Pad 800. The fluid communication enables thermal communication via the transport of thermal fluids 826 and 827 through various components of a fluid conveyance system, including fluid lines 825; pumps 811-812; solenoid valves 821-824; heat exchangers 818 and 828 and the like.

Cold pump 811 is always active. During a cold cycle fluid from this pump is included in a thermal therapy protocol specifying a temperature range and duration of thermal conditions applied via the thermal therapy pad 800 that are generally cooler than a specified hot cycle. During a transition period from a cold cycle to a hot cycle and during a hot cycle the cold pump 811 circulates fluid through the cold HX back to the cold tank keeping the cold fluid cold for the next cold cycle During the transition period from hot to cold, the cold pump pushes hot fluid from the pad 800 back to the hot tank.

Similarly, hot pump 812 is always active. During a hot cycle fluid from this pump is included in a thermal therapy protocol specifying a temperature range and duration of thermal conditions applied via the thermal therapy pad 800 that are generally hotter than a specified cold cycle. During a transition period from a hot cycle to a cold cycle and during a cold cycle the hot pump 811 circulates fluid through the hot tank/immersion heater 828 keeping the hot fluid hot for the next hot cycle During the transition period from cold to hot, the hot pump pushes cold fluid from the pad 800 back to the cold tank Solenoid valves 821-824 are operative to direct a flow of thermal fluid based upon a thermal therapy protocol. The thermal therapy protocol specifies a thermal condition to be experienced by a patient via conditions in the thermal therapy pad 800. The thermal condition may include a temperature for a period of time. Time instance may be tracked along a therapy time continuum that commences as a therapy session begins. Time instances included in the therapy time continuum may be associated with specific temperature and pressure to be experienced by the patient at a specific time instance. Solenoid included in the solenoid valves 821-824 may be activated to cause the conditions specified at a time instance to be experienced by the patient. Conditions experienced by the patient may include a rapid transition of thermal energy from one time instance to another based upon the methods and apparatus discussed herein, including a return of fluid 826-827 present in the thermal therapy pad 800 to a thermal fluid tank 801-802 supplying thermal fluid 826-827 prior to the rapid transition of thermal energy specified in a treatment protocol (or specified by a manual user command), until the transition in thermal energy has been accomplished (or a specified percentage of thermal energy transition has been accomplished, such as 80% or 90% of the thermal energy transition).

In some embodiments, an immersion heater 828 or other heating element may heat thermal fluid 827 in the Hot Tank 802. The immersion heater 828 may also be placed in the hot fluid line after the hot pump 812. Other heating means, such as a TE heat exchanger may also be used.

In some embodiments, a heat exchanger 818 may be used to change a temperature of thermal fluid 826-827. The heat exchanger may include one or more thermoelectric modules placed in thermal communication with the thermal fluid. The functioning of a thermoelectric heat exchanger allows it to be operative to change a temperature of the thermal fluid 826-27 to a hotter or cooler temperature within a very accurate tolerance.

Thermistors 813-815 may quantify a temperature of thermal fluid at various positions within the fluid communication channels 800-802, 811-818, 821-825 within the thermal therapy system 830. A user interface 819-820 may include a status of one or more conditions within the thermal therapy system 830, such as, for example, a level of fluid within the Cold Tank 801 and/or the Hot Tank 802. In some embodiments, the user interface 819-820 may be a visual window into a thermal fluid 826-827 level.

In addition, a Cold RTD 816 and a Hot RTD 817 are typically used to control the cold and hot fluid temperatures respectively. RTD's are preferred due to their long term stability.

Some embodiments may include an integrated sterilizer 829 to sterilize thermal fluid 826-827 and/or one or more aspects of the thermal therapy system 820. Sterilization may be accomplished by sterilizer 829 via exposure to ultraviolet light, chemical methods, ozone or other reactive gas, and/or a filter. Sterilization may be added to existing units by inserting a sterilizer in a fluid circulation loop, e.g., hot line 209b and/or cold line 210b.

Figure 10A:
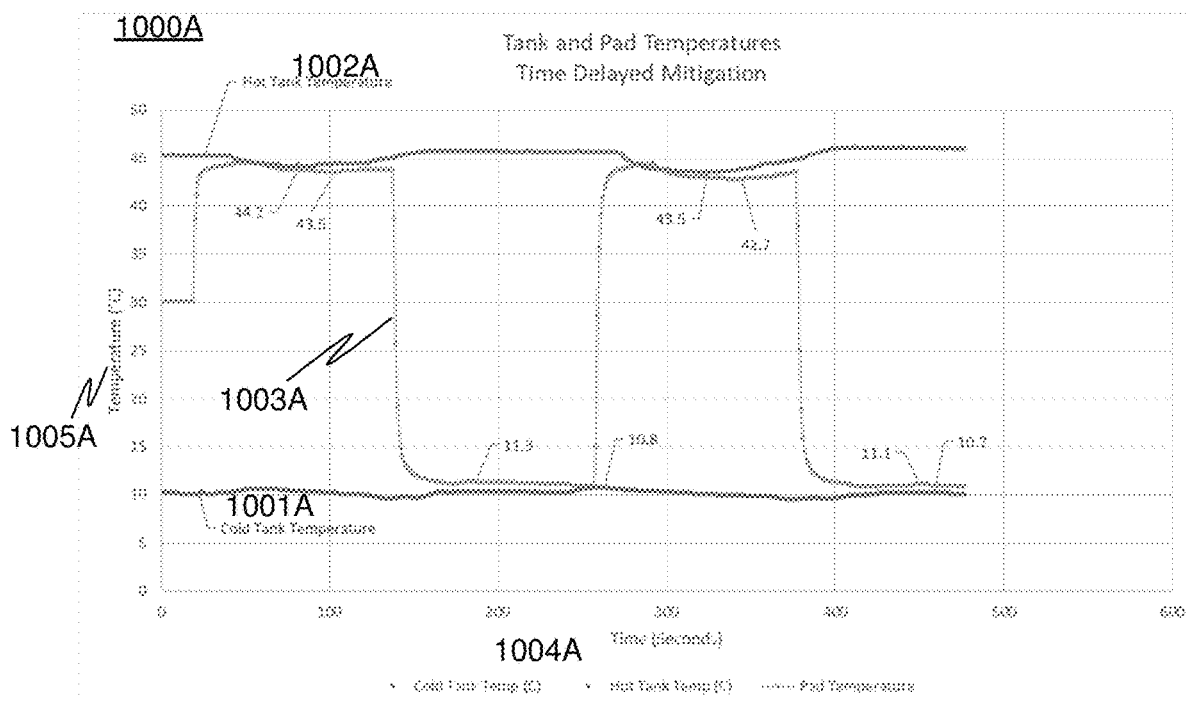
FIG. 10A illustrates a graph of temperatures present in a fluid storage tank and a thermal therapy pad during a thermal contrast cycle with time delayed mitigation processes presented herein being utilized.

Referring now to FIG. 10A, a graph 1000A quantifies respective temperatures 1005A of a Cold Tank 1001A and a Hot Tank 1002A during progression of a thermal therapy protocol including specified thermal pad temperatures 1003A along a time continuum 1004A. Of significance is the minimal variance of temperature following a transition of thermal pad temperature 1003A, such as those transitions that occur, for example, at time 20 seconds; time 140 seconds; time 260 seconds; and time 380 seconds. The minimal delta in tank temperatures 1001A-1002A in the graph 1000A result from time delayed mitigation. Similar results and sometimes better results are experienced from a transition based upon a temperature of thermal fluid returning to the tanks.

Figure 11:
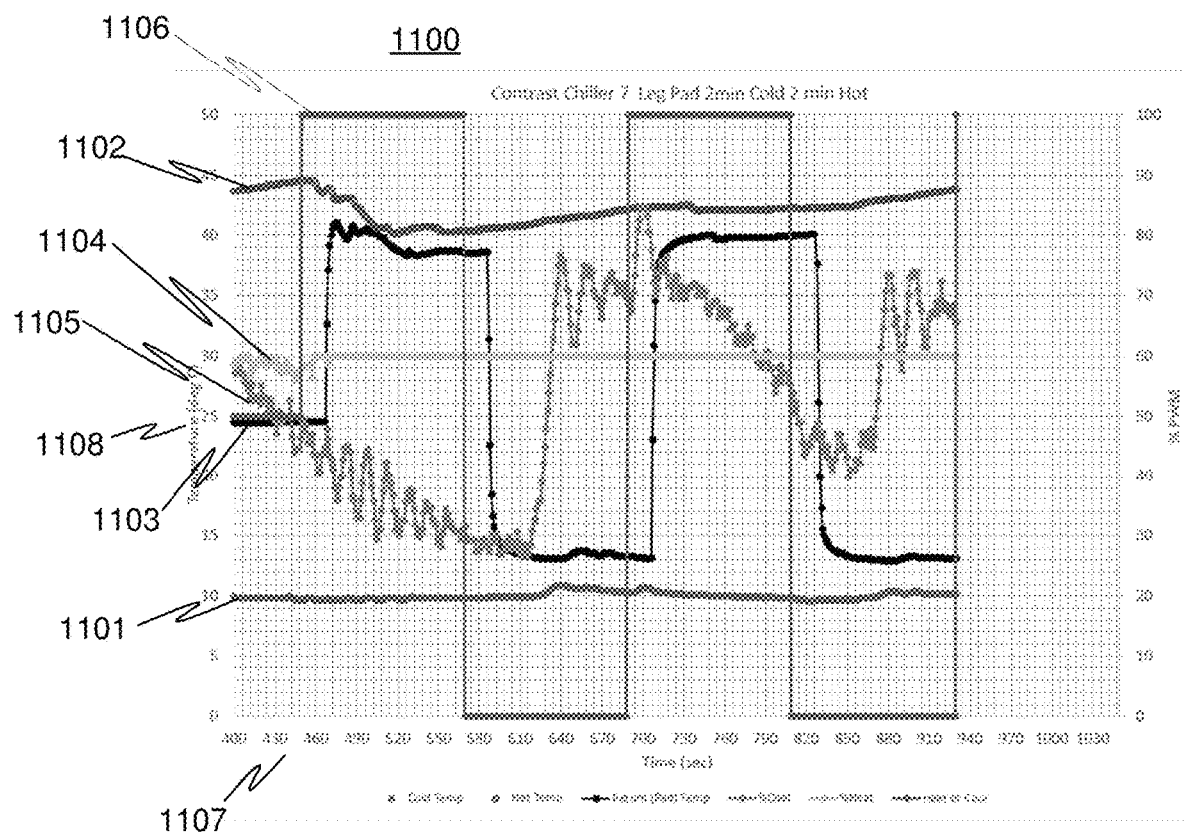
FIG. 11 illustrates a graph of temperatures present in a fluid storage tank and a thermal therapy pad during a thermal contrast cycle with temperature threshold based delay mitigation processes presented herein being utilized.

Referring now to FIG. 11, a graph quantifies a stableness of temperature 1108 of a Cold Tank 1101 and a Hot Tank 1102 over a continuum of time 1107 during which a thermal therapy protocol 1106 is administered. The graph 100 also indicates a temperature of fluid returning from the thermal therapy pad 1103 following circulation through a thermal therapy pad positioned on a body part portion (in this case, a thermal therapy pad wrapped around a human leg). A percentage of heating capacity 1104 and a percentage of cooling capacity 1105 is also indicated on the graph.

Referring now to FIGS. 9A-9D, multiple various views of a thermal fluid reservoir unit 900 are illustrated. According to the present invention, a thermal fluid reservoir unit 900 may include both a Hot Fluid Reservoir 902 and a Cold Fluid Reservoir 903. The Hot Fluid Reservoir 902 and a Cold Fluid Reservoir 903 may both be filled via a single filling spout 901. Accordingly, thermal fluid 904 may be poured, or otherwise provided to, the single filling spout 901 and then diverted to one or both of the hot fluid reservoir 902 and the cold fluid reservoir. A tank dividing wall 907 may separate the Hot Fluid Reservoir 902 and a Cold Fluid Reservoir 903. The tank dividing wall 907 may comprise a thermal insulating material and or be shaped to provide a air gap between the Hot Fluid Reservoir 902 and a Cold Fluid Reservoir 903.

Thermal fluid 904 in the thermal fluid reservoir unit 900 may naturally flow from one of the Hot Fluid Reservoir 902 and a Cold Fluid Reservoir 903 to the other upon reaching a level 908 equal to a top of the tank dividing wall 907. Thermal fluid within the thermal fluid reservoir unit 900 will therefore self-equilibrate and prevent overflowing of one of the Hot Fluid Reservoir 902 and a Cold Fluid Reservoir 903 while the other reservoir is less than full of thermal fluid. One or more first fluid ports 905 may be functional as an egress for thermal fluid 904 and therefore be functional to transport fluid out of the thermal fluid reservoir unit 900. One or more second fluid ports 906 may be functional as an ingress for thermal fluid 904 and therefore be functional to transport fluid into the thermal fluid reservoir unit 900. Alternatively, two separate fluid reservoirs with separate fill ports may be used.

Various embodiments may include multiple wraps specific to fluid channel/pump configurations. For example, after a baseball game (or during portions of the game that the pitcher is not active pitching, e.g., portions of an inning that the pitcher's team is at bat), a pitcher may have a first wrap on a pitching arm, and a second wrap on a leg.

Some embodiments may include multiple fluid loops within a single wrap, each fluid loop may have separately controlled pressure and/or temperature. In particular, wrap may be designed with specific areas of high/low pressure and high/low heat/cold. Control of individual specified areas of wrap, designs may include areas of heat in one portion of wrap and cold in another portion; areas of pressure in one area and areas of relief in another. For example, a single wrap around the upper arm may include a first pressure loop to provide a first amount of pressure and temperature therapy the bicep muscles, and a second pressure loop to provide a second amount of pressure and temperature therapy to triceps muscles.

Embodiments may include lines from a TEC unit to a thermal therapy wrap that includes both fluid channels and data conduits. Likewise, some embodiments may include pre-programmed thermal and/or pressure cycles on a per patient basis with patient identification, e.g., a finger scan or other biometric identifier (ID). In particular, therapy cycles may be controlled with respect to temperature profiles, pressure profiles, feedback loop and adjustment of individual specific aspects (e.g. pumps, valves, TEC unit) during therapy cycles, and compliance record of actual therapy applied.

Further, some embodiments may record location, time, date, and/or duration of therapy on a per patient basis with patient identification, e.g., a finger scan, biometric ID, unique identifier, etc. Specific embodiments may include control by use of a smart device (e.g., iPhone® or Android™ phone, tablet, etc.), and transmission to a data aggregator. In particular, embodiments may include aggregating data across multiple patients, location, age etc. Embodiments also may include remote control of therapy (e.g., therapy cycle profile being inputted by a practitioner from a remote site), and managing a universally unique identifier (UUID) of a therapeutic device.

Still further, some embodiments may include hot and/or cold temperature profiles according to a desired treatment plan on a per-patient basis with patient identification, e.g., finger scan, other biometric ID, unique identifier etc. In particular, profiles may include a therapy profile for injury, a profile to increase performance during sideline breaks of athletic performance, a profile to increase cognitive ability, and/or a profile to increase blood circulation during long sedentary periods, e.g., during airplane travel, sitting at a desk, laying in a hospital bed, etc.

Embodiments may combine temperature and/or pressure therapy with light therapy. In particular, light therapy may be applied in coordination with a thermal/pressure cycle, and/or to complement the objective of a thermal/pressure cycle. For example, a thermal/pressure cycle that heats and causes vasodilation may be complemented with light that also causes vasodilation, or the light may be removed during constriction thermal cycle, etc. Light therapy may increase adenosine triphosphate (ATP) production in synchrony with thermal cycle and/or pressure cycle. Light therapy may be applied at infrared, e.g., about 660-980 nanometer.

Embodiments may include magnetic application, and may be included in the thermal fluid being circulated. Light or magnetic therapy may be aligned with acupressure and/or acupuncture locations. The location of light or magnetic therapy may be detailed on a sleeve. The sleeve may be specific to a patient, so that a practitioner may mark a location of a therapeutic agent on a sleeve, and then therapy is applied according to the markings.

Some embodiments may include a therapeutic profile based upon biometric readings of a patient. This feature may be tied to activation of specific pumps, valves, etc. Parameters to monitor may include pulse rate, blood pressure, swelling, skin temperature, body temperature, temperature differential between skin and core body, and so forth.

In another aspect, multiple wraps on a single patient may be administered at once with a single TEC machine. The hydraulic and physical interface may be configured in parallel with "Y" fittings to circulate, and/or a manifold with separate on/off valves. Embodiments may include automatic control of valves. Alternatively, the hydraulic and physical interface may be configured to be serial, using fittings to extend a flow, e.g., to an ankle, a lower leg, an upper leg, a torso, a shoulder an arm, etc. Alternatively, an attachment mechanism may couple one pump to the next. The hydraulic and physical interface may include fluid communication, and physical fasteners such as a hook and loop fastener (i.e., Velcro™), snaps, etc.

Embodiments may include multiple patients treated with a single large TEC machine, in order to provide efficiency of scale, wherein one patient may receive cooling therapy while another patient simultaneously may receive heating therapy. When it is time for the temperature cycle to reverse, a valve may switch to change fluid flow.

Multiple patients may be treated in parallel, such that a control unit turns flow on or off to an individual patient or individual treatment area (or limited/fully open) depending upon conditions measured at individual patient or treatment area.

Embodiments may combine thermal, pressure, and light with pharmaceutical treatment. Synergistic benefits may include treatment timing (i.e., synchronization), coordinated dosage and duration. Embodiments take advantage of capillary constriction and dilation based upon thermal treatment. Treatments may be by topical application (i.e., transdermal based upon treatment site), or injection at site of therapy. Embodiments include treatment protocols based upon drug response to thermal, pressure, and light conditions, for example, a heat or light activated drug.

Embodiments may include topical gel or cream, in conjunction with optimized thermal, magnetic, and/or light transfer therapy. Embodiments may include pain relief, e.g., anesthesia such as lidocaine to reduce localized pain. Embodiments may include a therapeutic agent. Embodiments may include cleaning and germ treatment to preserve sterile integrity of equipment.

Embodiments combine contrast therapy with movement (i.e., physical therapy (PT)), which may include treatment before and/or after PT. Embodiments include tracking movement (e.g., accelerometer or image tracking), and matching movement and thermal application. Embodiments may record movement, biometrics, thermal condition, pressure, and/or other treatments as well as time, place, and patient, etc.

Embodiments may also include contrast therapy pad with Thermal electric tiles on a pad. For example, TEC tiles may be controlled individually or only in pre-defined areas. Fluid channels may be used to disperse excess heat or cold. In this case, fluid is needed only to add or remove heat, not to supply therapeutic temperature, and benefits may include less fluid required. Temperature sensors in the pad would be required in this embodiment. Embodiments may be associated with reservoirs of heated fluid and/or cooled fluid. These embodiments may be more efficient and provide a faster temperature transition. A gel and/or liner material or gel pack may be used to enhance the transfer of heat from the pad to the skin.

Embodiments may include a smart device controller for a TEC unit. Embodiments may display specific conditions pre-programmed in the TEC unit, and display conditions of treated area (e.g., pressure, temperature). Embodiments allow for remote monitoring of actual conditions. Embodiments are not limited to thermowraps, but instead may be applicable to other TEC devices. Embodiments may gather data in local data form, convert the data to Internet Protocol (IP) messages, transmit the IP messages to a remote monitoring station or server, and at the remote monitoring station or server convert the IP messages back to display format for displaying to a person, Embodiments may record time/place, may perform remote monitoring of status, and may monitor compliance with a treatment protocol.

Embodiments may provide data aggregation (big data) across multiple treatments and profiles. Big data is known in the art as extremely large data sets that may be analyzed computationally to reveal patterns, trends, and associations, especially relating to human behavior and interactions. As applied to therapy, big data aggregation may help identify beneficial treatment regimes.

Embodiments may be combined with physical therapy motion monitoring, e.g., motion monitoring of a limb, while the patient is upright, reclined, or supine. Embodiments may monitor compliance with a therapy protocol, and may allow the compliance to be viewed remotely, e.g., by a health care provider or by the patient.

Figure 12:
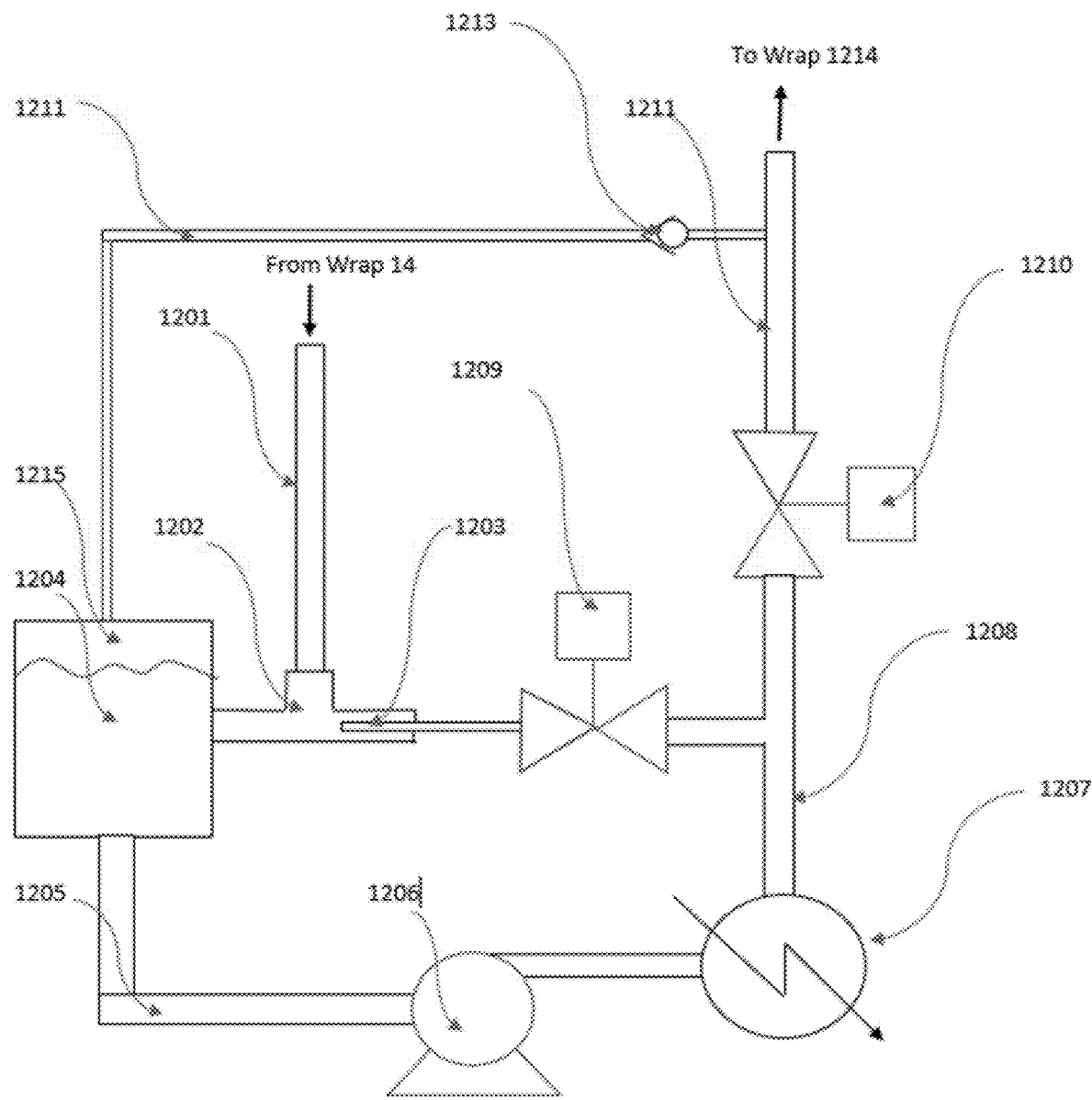
FIG. 12 illustrates methods for purging a thermal therapy wrap according to some embodiments of the present invention.

Referring now to FIG. 12, another aspect of the present invention includes methods for purging a thermal therapy wrap 1214 of thermal fluid for storage while the thermal therapy pad 1214 is not in use.

After strenuous exercise or after injury/surgery, thermal therapy involving application of contrasting heating and cooling to mammalian tissue, may be implemented to speed recovery. The present invention includes multiple methods and apparatus for accomplishing such thermal therapy using a wrap containing fluid channels through which a hot or cold fluid is pumped. These methods allows precise control of the therapy temperature, providing superior results.

When a thermal therapy treatment is completed a thermal therapy wrap typically contains a significant quantity of thermal fluid. It is desirable to remove this fluid prior to storing the wrap. Removal of the thermal fluid from the thermal therapy wrap allows for ease of storage and substantially reduces the thermal therapy pad's weight. One aspect of the present invention provides a novel way to remove this fluid, a method that does not require the use of compressed air or vacuum apparatus, but instead uses the pump that conveys thermal fluid to the thermal therapy wrap during a thermal therapy procedure to be used to also remove fluid from the wrap prior to its storage.

As discussed herein, in some exemplary embodiments, a thermal therapy protocol may include multiple thermal therapy procedures or method steps. During a thermal therapy method step of procedure (either heating or cooling) fluid flows from Reservoir 1204 to Pump 1206 through thermal fluid channel (such as a tube) 1205. Pump 1206 pumps the fluid into heat exchanger 1207 through a Tube 1208 to open Solenoid Valve 1210 and then to the Thermal Therapy wrap 1214. From the Therapy wrap 1214 the fluid returns to the Reservoir 1204 via return Tube 1201 and Venturi Tee 1202.

When a thermal therapy method step or protocol procedure is complete, Solenoid Valve 1210 may close and Solenoid Valve 1209 may open, causing fluid to flow through Venturi Nozzle 1203. Venturi Nozzle 1203 causes high velocity fluid to flow through Venturi TEE 1202, creating a negative suction pressure in return tube 1201 which in turn pull fluid out of Wrap 1214.

If Reservoir 1204 is not vented, then air line 1211 from the air space above the Reservoir 1204 may, for example be connected to a Wrap 1204 supply tube 1211 through a Check Valve 1213 to allow fluid returning to Reservoir 1204 to displace the air in space 1215. The Check Valve 1213 is thereby operative to prevent fluid from by-passing the Wrap 1214 during the thermal therapy method step or procedure and flowing directly back to the Reservoir 1204.

A number of embodiments of the present invention have been described. Nevertheless, it will be understood that various modifications may be made without departing from the spirit and scope of the invention. For example, various methods or equipment may be used to implement the process steps described herein or to create a device according to the inventive concepts provided above and further described in the claims. In addition, various integration of components, as well as software and firmware may be implemented. Accordingly, other embodiments are within the scope of the following claims.

While the foregoing is directed to embodiments of the present disclosure, other and further embodiments of the present disclosure may be devised without departing from the basic scope thereof. It is understood that various embodiments described herein may be utilized in combination with any other embodiment described, without departing from the scope contained herein. Further, the foregoing description is not intended to be exhaustive or to limit the disclosure to the precise form disclosed. Modifications and variations are possible in light of the above teachings or may be acquired from practice of the disclosure. Certain exemplary embodiments may be identified by use of an open-ended list that includes wording to indicate that the list items are representative of the embodiments and that the list is not intended to represent a closed list exclusive of further embodiments. Such wording may include "e.g.," "etc.," "such as," "for example," "and so forth," "and the like," etc., and other wording as will be apparent from the surrounding context.

No element, act, or instruction used in the description of the present application should be construed as critical or essential to the disclosure unless explicitly described as such. Also, as used herein, the article "a" is intended to include one or more items. Where only one item is intended, the term "one" or similar language is used. Further, the terms "any of" followed by a listing of a plurality of items and/or a plurality of categories of items, as used herein, are intended to include "any of," "any combination of," "any multiple of," and/or "any combination of" multiples of the items and/or the categories of items, individually or in conjunction with other items and/or other categories of items.

Moreover, the claims should not be read as limited to the described order or elements unless stated to that effect. In addition, use of the term "means" in any claim is intended to invoke 35 U.S.C. § 112(f), and any claim without the word "means" is not so intended.

What is claimed is:

1. A contrast therapy apparatus to provide controlled therapeutic treatments, comprising:
   a thermal pad, comprising:
   a fluidic channel having an input port and an output port; and
   a thermally-transmissive outer covering; and
   a control unit, comprising:
   a fluid channel output port coupled to the input port of the thermal pad fluidic channel;
   a fluid channel input port coupled to the output port of the thermal pad fluidic channel;
   one or both of a hot-fluid circulation loop coupled to the output port and the input port and a cold-fluid circulation loop coupled to the output port and the input port;
   a pump to provide fluid flow in at least one of the hot-fluid circulation loop and the cold-fluid circulation loop;
   a processor coupled to a memory, the processor configured to execute instructions stored in the memory, to provide to the thermal pad a fluid flow having a predetermined temperature profile;
   one or more diverting valves operative to cause hot fluid to flow out of a hot fluid reservoir and into the thermal pad, and flow out of the thermal pad into a cold fluid reservoir during a cold to hot transition delay period, and the hot fluid to flow out of the hot fluid reservoir and into the thermal pad, and flow out of the thermal pad into the hot fluid reservoir during a hot cycle that follows the cold to hot transition delay period; and
   a solenoid valve at each end of therapy pad, the diverting valves operative to divert fluid from flowing into the input port of the thermal pad to flowing to a Venturi that provides suction pressure to remove fluid from the wrap.

2. The contrast therapy apparatus of claim 1, further comprising separate pumps for the hot-fluid circulation loop and the cold-fluid circulation loop.

3. The contrast therapy apparatus of claim 1, wherein the one or more diverting valves comprise one or more hot valves to couple the hot-fluid circulation loop to the therapy pad and one or more cold valves to couple the cold-fluid circulation loop to the therapy pad, said one or more hot valves and the one or more cold valves operative to cause cold fluid to flow out of the cold fluid reservoir and into the thermal pad, and flow out of the thermal pad into the hot fluid reservoir during a hot to cold transition delay period, and the cold fluid to flow out of the cold fluid reservoir and into the thermal pad, and flow out of the thermal pad into the cold fluid reservoir during a cold thermal cycle which follows the hot to cold transition delay period.

4. The contrast therapy apparatus of claim 3 wherein a flow of cold fluid out of the cold fluid reservoir and into the thermal pad, and flow out of the thermal pad into the hot fluid reservoir during the hot to cold transition delay period improves stability of the cold fluid reservoir during the cold thermal cycle by reducing a change of temperature change in the cold fluid reservoir as compared to a change in temperature in the cold fluid reservoir without a transition delay period comprising returning fluid from the cold fluid reservoir into the hot fluid reservoir.

5. The contrast therapy apparatus of claim 4 wherein one or both of the hot to cold transition delay period and the cold to hot transition delay period is based upon a size of the thermal pad.

6. The contrast therapy apparatus of claim 5 where one or more of the hot to cold transition delay period or the cold to hot transition delay period comprises between 5 seconds and 90 seconds.

7. The contrast therapy apparatus of claim 6 where one or more of the hot to cold transition delay period or the cold to hot transition delay period comprises between 15 seconds and 40 seconds.

8. The contrast therapy apparatus of claim 6 wherein a flow rate of fluid through the thermal pad comprises between about 0.5 to 2 liters per minute.

9. The contrast therapy apparatus of claim 6 wherein a flow rate of fluid through the thermal pad comprises between about 0.8 and 1.2 liters per minute.

10. The contrast therapy apparatus of claim 6 additionally comprising a temperature sensor measuring a temperature of fluid in one or both of the hot-fluid circulation loop and the cold-fluid circulation loop.

11. The contrast therapy apparatus of claim 10 wherein one or more of the hot to cold transition delay time or the cold to hot transition delay time is determined by measuring a returning fluid temperature with the temperature sensor and actuating return side diverting valves when a measured return side temperature reaches a pre-determined threshold.

12. The contrast therapy apparatus of claim 11 wherein the pre-determined threshold occurs when return side temperature changes in an amount of between about 2° C. and 20° C. from a normal return side treatment temperature.

13. The contrast therapy apparatus of claim 11 wherein the pre-determined threshold occurs when return side temperature changes in an amount of between about 7° C. and 13° C. from a normal return side treatment temperature.

14. The contrast therapy apparatus of claim 10 wherein one or both of the hot to cold transition delay period or the cold to hot transition delay period is determined by measuring a temperature of returning fluid with the temperature sensor and actuating return side diverting valves when the measured return side temperature change meets a pre-determined rate of change.

15. The contrast therapy apparatus of claim 14 wherein the pre-determined rate of change is between about 0.01° C/sec and 0.2° C/sec.

16. The contrast therapy apparatus of claim 14 wherein the pre-determined rate of change is between about 0.01° C/sec and 2.0° C/sec.

17. The contrast therapy apparatus of claim 14 wherein the pre-determined rate of change is between about 0.5° C/sec and 1.5° C/sec.

18. The contrast therapy apparatus of claim 3 wherein one or both of the hot to cold transition delay period and the cold to hot transition delay period is based upon a type of thermal pad through which fluid is circulated.

19. The contrast therapy apparatus of claim 1 wherein a flow of hot fluid out of the hot fluid reservoir and into the thermal pad, and flow out of the thermal pad into the cold fluid reservoir during the cold to hot transition delay period improves stability of the hot fluid reservoir during a hot thermal cycle by reducing a change of temperature change in the hot fluid reservoir as compared to a change in a temperature in the hot fluid reservoir without a transition delay period comprising returning fluid from the hot fluid reservoir into the cold fluid reservoir.

20. The contrast therapy apparatus of claim 1 additionally comprising tubing attached to each valve, the tubing size comprising a ¼" inside diameter and a flow rate through the venturi is between about 1 liters per minute and 2 liters per minute.

* * * * *